United States Patent
Yanai et al.

(10) Patent No.: US 7,109,018 B1
(45) Date of Patent: Sep. 19, 2006

(54) TRANSFORMANT PRODUCING SECONDARY METABOLITE MODIFIED WITH FUNCTIONAL GROUP AND NOVEL BIOSYNTHESIS GENES

(75) Inventors: Koji Yanai, Odawara (JP); Kaoru Okakura, Odawara (JP); Shohei Yasuda, Odawara (JP); Manabu Watanabe, Odawara (JP); Koichi Miyamoto, Odawara (JP); Naoki Midoh, Odawara (JP); Takeshi Murakami, Odawara (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 280 days.

(21) Appl. No.: 10/089,514

(22) PCT Filed: Sep. 29, 2000

(86) PCT No.: PCT/JP00/06783

§ 371 (c)(1),
(2), (4) Date: Mar. 29, 2002

(87) PCT Pub. No.: WO01/23542

PCT Pub. Date: Apr. 5, 2001

(30) Foreign Application Priority Data

Sep. 29, 1999 (JP) ................................. 11-276314

(51) Int. Cl.
*C12N 1/20* (2006.01)
*C12N 5/10* (2006.01)
*C07H 21/04* (2006.01)

(52) U.S. Cl. .............................. 435/252.3; 435/320.1; 536/23.1; 530/350

(58) Field of Classification Search ............. 435/252.3, 435/410, 320.1; 536/23.1; 530/350
See application file for complete search history.

(56) References Cited

U.S. PATENT DOCUMENTS

| | | | | |
|---|---|---|---|---|
| 2,990,325 | A | * | 6/1961 | Donovick et al. .......... 424/122 |
| 5,763,221 | A | | 6/1998 | Aoyagi et al. |
| 2002/0072062 | A1 | * | 6/2002 | Paradkar et al. ................ 435/6 |

FOREIGN PATENT DOCUMENTS

| EP | 0 634 408 | 1/1995 |
|---|---|---|
| EP | 0 685 469 | 12/1995 |
| EP | 0 903 347 | 9/1996 |
| EP | 0 780 468 | 6/1997 |
| EP | 0 930 304 | 7/1999 |
| WO | 96/01901 | 1/1996 |
| WO | 97/00944 | 1/1997 |
| WO | 97/11064 | 3/1997 |
| WO | 97/20945 | 6/1997 |

OTHER PUBLICATIONS

GenBank Accession No. U21728 (1996) *Streptomyces venezuelae* p-aminobenzoic acid synthase (pabAB) gene.*

GenBank Accession No. AAB30312 (1996) p-aminobenzoic acid synthase [*Streptomyces venezuelae*].*

He et al. The gene clsuter for chloramphenicol biosynthesis in *Streptomyces venezuelae* ISP5230 includes novel shikimate pathway homolgues and a monomodular non-ribosomal peptide synthetase gene. Microbiology (2001) 147: 2817-2829.*

GenBank Accession No. AF262220 (Oct., 2000) *Streptomyces venezuelae* chloramphenicol biosynthetic gene cluster, partial sequence.*

Miyadoh et al. Taxonomic position of the fungus producing the anthelmintic PF1022 based on the 18S rRNA gene base sequence. Nippon Kingakkai Kaiho (2000) 41(4): 183-188 (Abstract only).*

Yanai et al. Para-position derivatives of fungal anthelmintic cyclodepsipeptides engineered with *Streptomyces venezuelae* antibiotic biosynthetic genes. Nature Biotechnology (2004) 22(7): 848-855.*

Michael P. Brown et al., "A role for pabAB, a p-aminobenzoate synthase gene of *Streptomyces venezuelae* ISP5230, in chloramphenicol biosynthesis", Microbiology 142, pp. 1345-1355 (1996).

V. Blanc et al., "Identification and analysis of gened from *Streptomyces pristinaespiralis* encoding enzymes involved in the biosynthesis of the 4-dimethylamino-L-phenylalanine precursor of pristinamycin I", Molecular Microbiology, vol. 23, No. 2, pp. 191-202, 1997.

J. Doull et al., "Isolation and Characterization of *Streptomyces venezuelae* Mutants Blocked in Chloramphenicol Biosynthesis" Journal of General Microbiology, vol. 131, pp. 97-104, 1985.

(Continued)

*Primary Examiner*—Chih-Minh Kam
(74) *Attorney, Agent, or Firm*—Wenderoth, Lind & Ponack, L.L.P.

(57) ABSTRACT

An objective of the present invention is to provide a transformant altered so as to produce a secondary metabolite in which a benzene ring of the secondary product is modified at the para-position with a functional group containing a nitrogen atom. A transformant according to the present invention is a transformant of an organism producing a secondary metabolite having a benzene ring skeleton without substitution at the para-position with a functional group containing a nitrogen atom, said transformant being transformed by introducing genes involved in a biosynthetic pathway from chorismic acid to p-aminophenylpyruvic acid, including a gene encoding an amino acid sequence (SEQ ID NO: 2) having 4-amino-4-deoxychorismic acid synthase activity, a gene encoding an amino acid sequence (SEQ ID NO: 4) having 4-amino-4-deoxychorismic acid mutase activity and a gene encoding an amino acid sequence (SEQ ID NO: 6) having 4-amino-4-deoxyprephenic acid dehydrogenase activity, so as to produce a secondary metabolite having a benzene ring skeleton substituted at the para-position with a functional group containing a nitrogen atom. Another objective of the present invention is to provide a novel gene involved in the biosynthetic pathway from chorismic acid to p-aminophenylpyruvic acid. A novel gene according to the present invention comprises genes encoding the amino acid sequences of SEQ ID NOs: 2, 4 and 6 or modified sequences thereof.

19 Claims, 12 Drawing Sheets

OTHER PUBLICATIONS

M.P. Brown et al., "A role for pabAB, a p-aminobenzoate synthase gene of *Streptomyces venezuelae* ISP5230, in chloramphenicol biosynthesis", *Microbiol.*, vol. 142, pp. 1345-1355, (1996).

B.P. Nichols et al., "para-Aminobenzoate Synthesis from Chorismate Occurs in Two Steps", *Journal of Biological Chemistry*, vol. 264, No. 15, pp. 8597-8601, (1989).

* cited by examiner

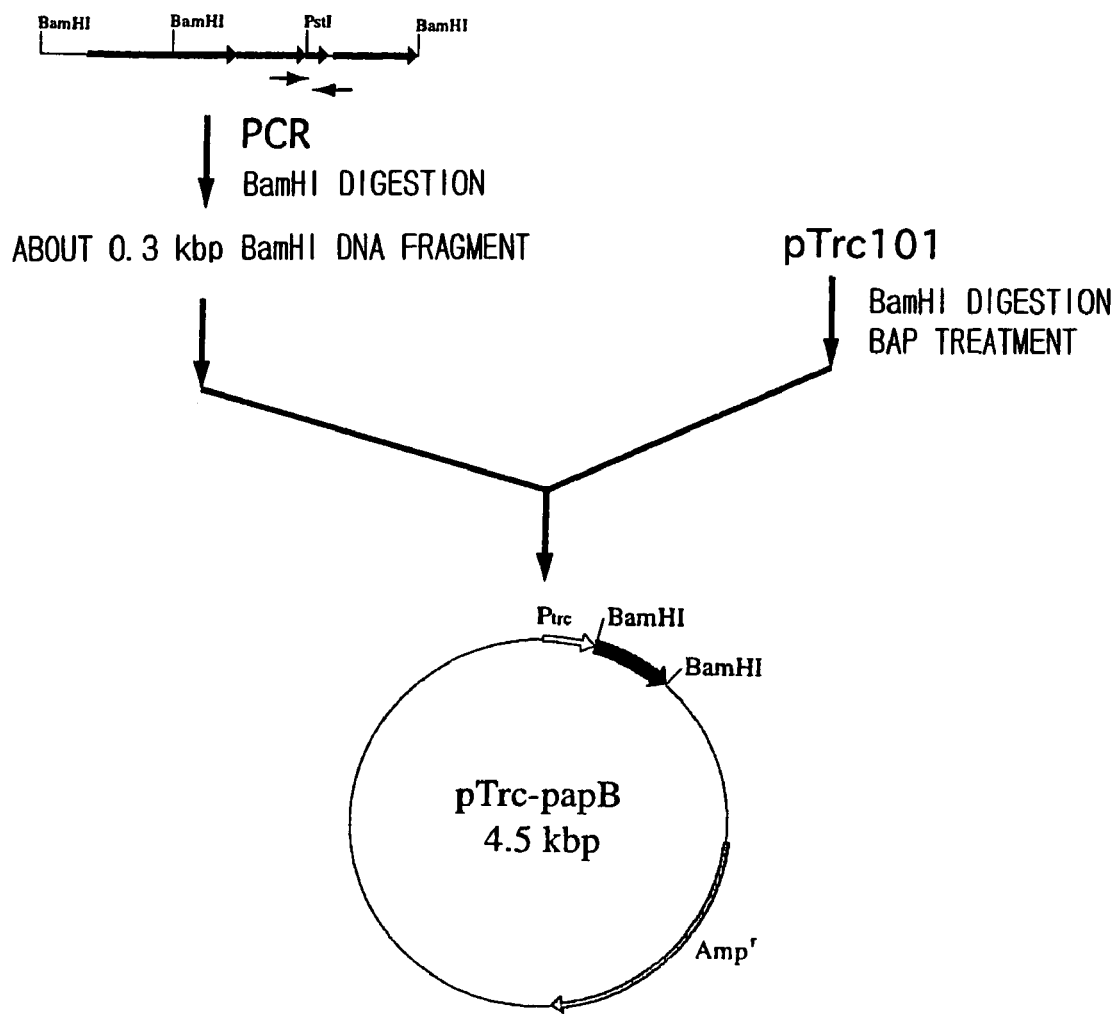
F I G. 4

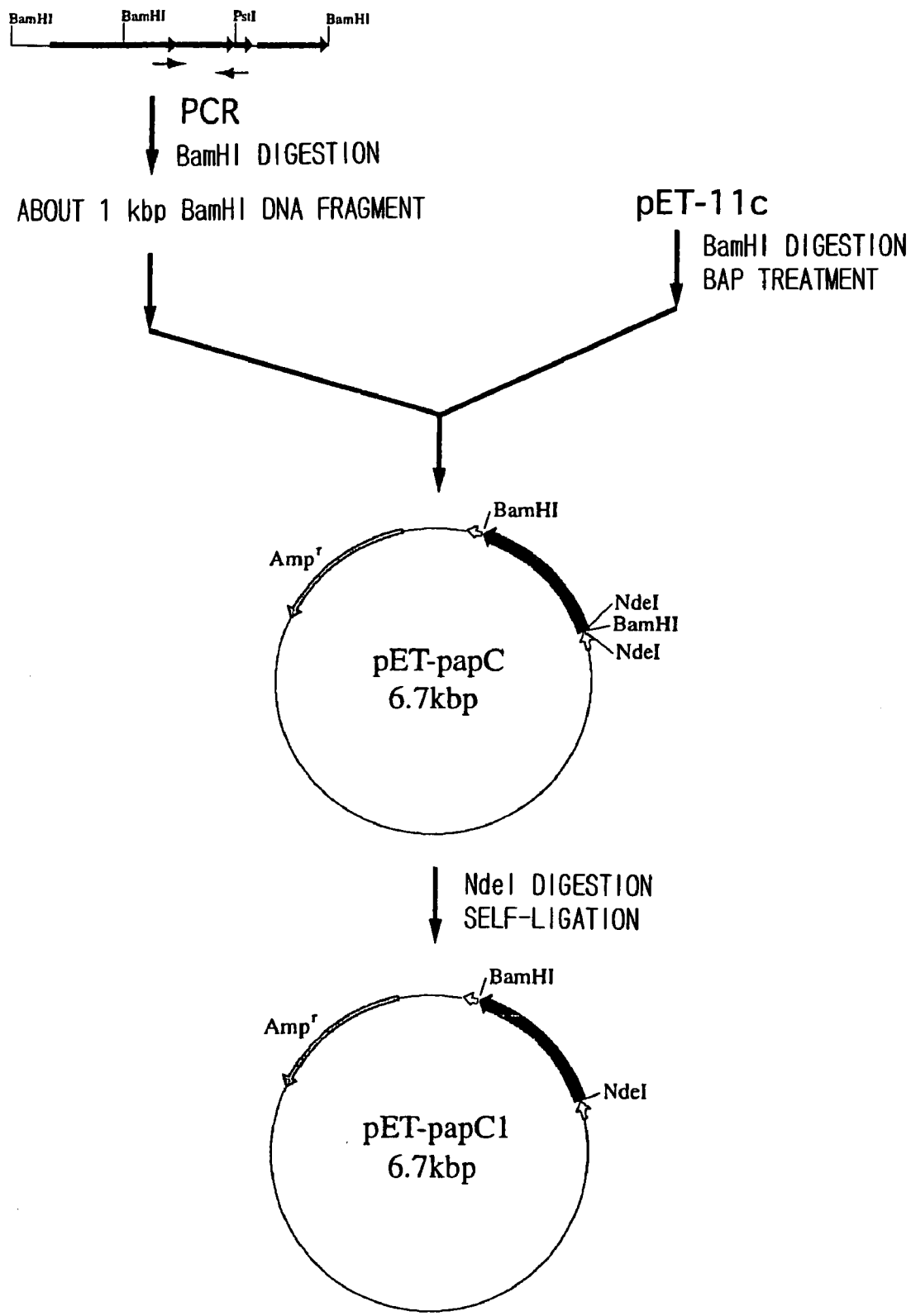
F I G. 6

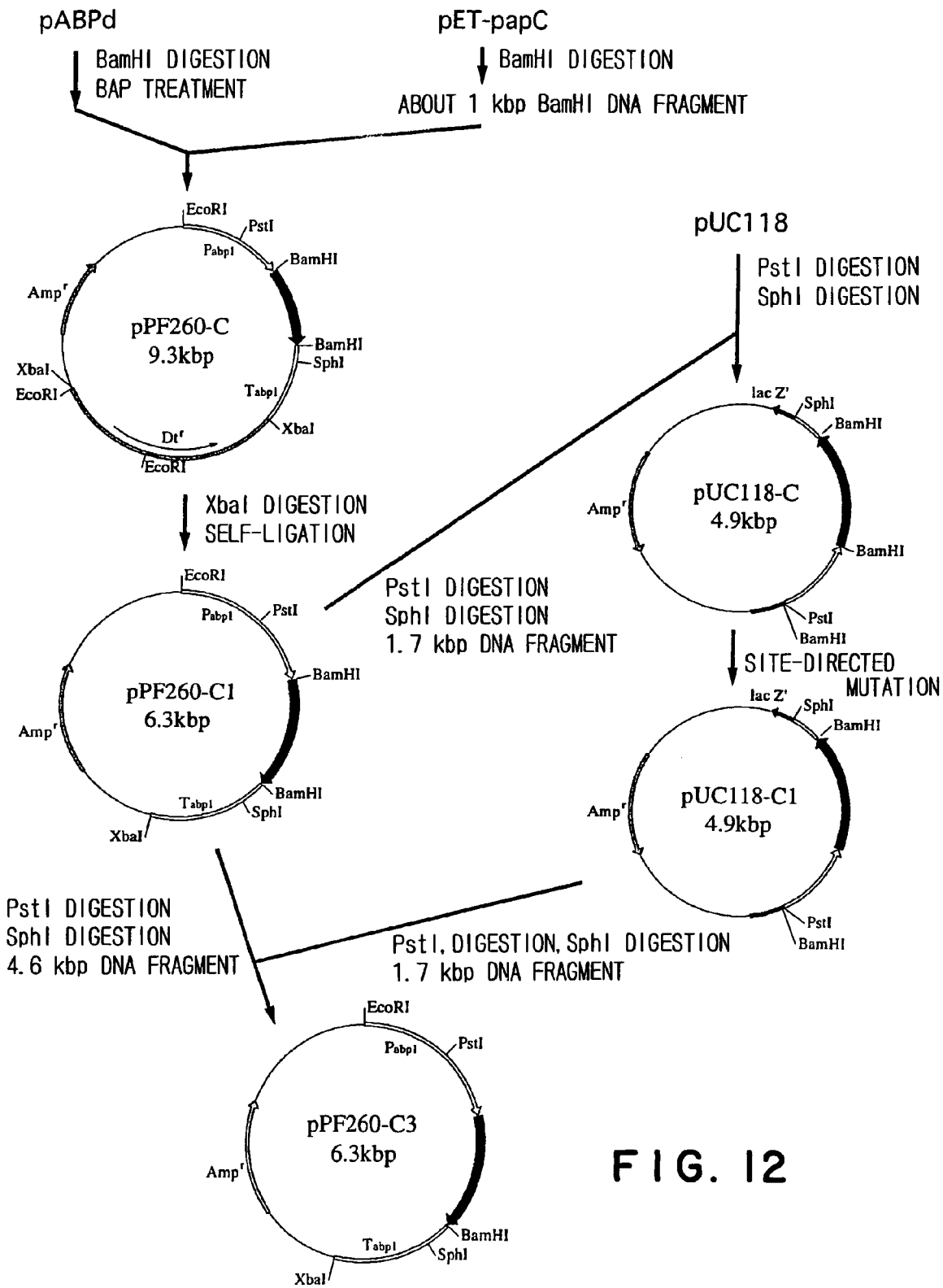
F I G. 12

SEQUENCE LISTING

```
<160> NUMBER OF SEQ ID NOS: 23

<210> SEQ ID NO 1
<211> LENGTH: 2061
<212> TYPE: DNA
<213> ORGANISM: Streptomyces venezuelae
<220> FEATURE:
<221> NAME/KEY: CDS
<222> LOCATION: (1)..(2058)

<400> SEQUENCE: 1 atg cgc acg ctt ctg atc gac aac tac gac tcg ttc acc cac aac ctg      48
Met Arg Thr Leu Leu Ile Asp Asn Tyr Asp Ser Phe Thr His Asn Leu
  1               5                  10                  15 ttc cag tac atc ggc gag gcc acc ggg caa ccc ccc gtc gtc gtg ccc      96
Phe Gln Tyr Ile Gly Glu Ala Thr Gly Gln Pro Pro Val Val Val Pro
             20                  25                  30 aac gac gcc gac tgg tcg cgg ctg ccc gtc gag gac ttc gac gcg atc     144
Asn Asp Ala Asp Trp Ser Arg Leu Pro Val Glu Asp Phe Asp Ala Ile
         35                  40                  45 gtc gtg tcc ccg ggc ccc ggc agc ccc gac cgg gaa cgg gac ttc gga     192
```

```
Val Val Ser Pro Gly Pro Gly Ser Pro Asp Arg Glu Arg Asp Phe Gly
     50                  55                  60 atc agc cgc cgg gcg atc acc gac agc ggc ctg ccc gtc ctc ggc gtc      240
Ile Ser Arg Arg Ala Ile Thr Asp Ser Gly Leu Pro Val Leu Gly Val
 65                  70                  75                  80 tgc ctc ggc cac cag ggc atc gcc cag ctc ttc ggc gga acc gtc ggc      288
Cys Leu Gly His Gln Gly Ile Ala Gln Leu Phe Gly Gly Thr Val Gly
                 85                  90                  95 ctc gcc ccg gaa ccc atg cac ggc cgg gtc tcc gag gtg cgg cac acc      336
Leu Ala Pro Glu Pro Met His Gly Arg Val Ser Glu Val Arg His Thr
            100                 105                 110 ggc gag gac gtc ttc cgg ggc ctc ccc tcg ccg ttc acc gcc gtg cgc      384
Gly Glu Asp Val Phe Arg Gly Leu Pro Ser Pro Phe Thr Ala Val Arg
            115                 120                 125 tac cac tcc ctg gcc gcc acc gac ctc ccc gac gag ctc gaa ccc ctc      432
Tyr His Ser Leu Ala Ala Thr Asp Leu Pro Asp Glu Leu Glu Pro Leu
130                 135                 140 gcc tgg agc gac gac ggg gtc gtc atg ggc ctg cgg cac cgc gag aag      480
Ala Trp Ser Asp Asp Gly Val Val Met Gly Leu Arg His Arg Glu Lys
145                 150                 155                 160 ccg ctg tgg ggc gtc cag ttc cac ccg gag tcc atc ggc agc gac ttc      528
Pro Leu Trp Gly Val Gln Phe His Pro Glu Ser Ile Gly Ser Asp Phe
                165                 170                 175 ggc cgg gag atc atg gcc aac ttc cgc gac ctc gcc ctc gcc cac cac      576
Gly Arg Glu Ile Met Ala Asn Phe Arg Asp Leu Ala Leu Ala His His
            180                 185                 190 cgg gca cgg cgc cac ggg gcc gac tcc ccg tac gaa ctc cac gtg cgc      624
Arg Ala Arg Arg His Gly Ala Asp Ser Pro Tyr Glu Leu His Val Arg
            195                 200                 205 cgc gtc gac gtg ctg ccg gac gcc gaa gag gta cgc cgc ggc tgc ctg      672
Arg Val Asp Val Leu Pro Asp Ala Glu Glu Val Arg Arg Gly Cys Leu
            210                 215                 220 ccc ggc gag ggc acc acg ttc tgg ctg gac agc agc tcc gtc ctc gaa      720
Pro Gly Glu Gly Thr Thr Phe Trp Leu Asp Ser Ser Ser Val Leu Glu
225                 230                 235                 240 ggc gcc tcg cgc ttc tcc ttc ctc ggc gac gac cgc ggc ccg ctc gcc      768
Gly Ala Ser Arg Phe Ser Phe Leu Gly Asp Asp Arg Gly Pro Leu Ala
                245                 250                 255 gag tac ctc acc tac cgc gtc gcc gac ggc gtc gtc tcc gtc cgc ggc      816
Glu Tyr Leu Thr Tyr Arg Val Ala Asp Gly Val Val Ser Val Arg Gly
            260                 265                 270 tcc gac ggc acc acg acc cgg acg cgg cgc ccc ttc ttc aac tac ctg      864
Ser Asp Gly Thr Thr Thr Arg Thr Arg Arg Pro Phe Phe Asn Tyr Leu
            275                 280                 285 gag gag cag ctc gaa cgc cga cgg gtc ccc gtc gcc ccc gaa ctg ccc      912
Glu Glu Gln Leu Glu Arg Arg Arg Val Pro Val Ala Pro Glu Leu Pro
290                 295                 300 ttc gag ttc aac ctc ggc tac gtc ggc tac ctc ggc tac gag ctg aag      960
Phe Glu Phe Asn Leu Gly Tyr Val Gly Tyr Leu Gly Tyr Glu Leu Lys
305                 310                 315                 320 gcg gag acc acc ggc gac ccc gcg cac cgg tcc ccg cac ccc gac gcc     1008
Ala Glu Thr Thr Gly Asp Pro Ala His Arg Ser Pro His Pro Asp Ala
                325                 330                 335 gcg ttc ctc ttc gcc gac cgc gcc atc gcc ctc gac cac cag gaa ggc     1056
Ala Phe Leu Phe Ala Asp Arg Ala Ile Ala Leu Asp His Gln Glu Gly
            340                 345                 350 tgc tgc tac ctg ctg gcc ctc gac cgc cgg ggc cac gac gac ggc gcc     1104
Cys Cys Tyr Leu Leu Ala Leu Asp Arg Arg Gly His Asp Asp Gly Ala
            355                 360                 365
```

```
cgc gcc tgg ctg cgg gag acg gcc gag acc ctc acc ggc ctg gcc gtc      1152
Arg Ala Trp Leu Arg Glu Thr Ala Glu Thr Leu Thr Gly Leu Ala Val
    370                 375                 380 cgc gcc ccg gcc gag ccg acc ccc gcc atg gtc ttc ggg atc ccc gag      1200
Arg Ala Pro Ala Glu Pro Thr Pro Ala Met Val Phe Gly Ile Pro Glu
385                 390                 395                 400 gcg gcg gcc ggc ttc ggc ccc ctg gcc cgc gcg cgc cac gac aag gac      1248
Ala Ala Ala Gly Phe Gly Pro Leu Ala Arg Ala Arg His Asp Lys Asp
                405                 410                 415 gcc tac ctc aag cgc atc gac gag tgc ctc aag gag atc cgc aac ggc      1296
Ala Tyr Leu Lys Arg Ile Asp Glu Cys Leu Lys Glu Ile Arg Asn Gly
            420                 425                 430 gag tcg tac gag atc tgc ctg acc aac atg gtc acc gcg ccg acc gag      1344
Glu Ser Tyr Glu Ile Cys Leu Thr Asn Met Val Thr Ala Pro Thr Glu
        435                 440                 445 gcg acg gcc ctg ccg ctc tac tcc gcg ctg cgc gcc atc agc ccc gtc      1392
Ala Thr Ala Leu Pro Leu Tyr Ser Ala Leu Arg Ala Ile Ser Pro Val
    450                 455                 460 ccg tac ggc gcc ctg ctc gag ttc ccc gaa ctg tcg gtg ctg agc gcc      1440
Pro Tyr Gly Ala Leu Leu Glu Phe Pro Glu Leu Ser Val Leu Ser Ala
465                 470                 475                 480 tcg ccc gag cgg ttc ctc acg atc ggc gcc gac ggc ggc gtc gag tcc      1488
Ser Pro Glu Arg Phe Leu Thr Ile Gly Ala Asp Gly Gly Val Glu Ser
                485                 490                 495 aag ccc atc aag ggg acc cgc ccc cgg ggc ggc acc gcg gag gag gac      1536
Lys Pro Ile Lys Gly Thr Arg Pro Arg Gly Gly Thr Ala Glu Glu Asp
            500                 505                 510 gag cgg ctc cgc gcc gac ctg gcc ggc cgg gag aag gac cgg gcc gag      1584
Glu Arg Leu Arg Ala Asp Leu Ala Gly Arg Glu Lys Asp Arg Ala Glu
        515                 520                 525 aac ctg atg atc gtc gac ctg gtc cgc aac gac ctc aac agc gtc tgc      1632
Asn Leu Met Ile Val Asp Leu Val Arg Asn Asp Leu Asn Ser Val Cys
    530                 535                 540 gcg atc ggc tcc gtc cac gtg ccc cgg ctc ttc gag gtg gag acc tac      1680
Ala Ile Gly Ser Val His Val Pro Arg Leu Phe Glu Val Glu Thr Tyr
545                 550                 555                 560 gcg ccc gtg cac cag ctg gtg tcg acc atc cgg gga cgg ctg cgg ccc      1728
Ala Pro Val His Gln Leu Val Ser Thr Ile Arg Gly Arg Leu Arg Pro
                565                 570                 575 ggc acc agc acc gcc gcc tgc gta cgc gcc gcc ttc ccc ggc ggc tcc      1776
Gly Thr Ser Thr Ala Ala Cys Val Arg Ala Ala Phe Pro Gly Gly Ser
            580                 585                 590 atg acc ggc gcg ccc aag aag cgc acc atg gag atc atc gac cgc ctg      1824
Met Thr Gly Ala Pro Lys Lys Arg Thr Met Glu Ile Ile Asp Arg Leu
        595                 600                 605 gag gaa ggc ccc cgg ggc gtc tac tcc ggg gcg ctc gga tgg ttc gcc      1872
Glu Glu Gly Pro Arg Gly Val Tyr Ser Gly Ala Leu Gly Trp Phe Ala
    610                 615                 620 ctc agc ggc gcc gcc gac ctc agc atc gtc atc cgc acc atc gtg ctg      1920
Leu Ser Gly Ala Ala Asp Leu Ser Ile Val Ile Arg Thr Ile Val Leu
625                 630                 635                 640 gcc gac ggc cag gcg gag ttc ggc gtc ggc ggg gcg atc gtg tcc ctc      1968
Ala Asp Gly Gln Ala Glu Phe Gly Val Gly Gly Ala Ile Val Ser Leu
                645                 650                 655 tcc gac cag gag gag gag ttc acc gag acc gtg gta aag gcc cgc gcc      2016
Ser Asp Gln Glu Glu Glu Phe Thr Glu Thr Val Val Lys Ala Arg Ala
            660                 665                 670 atg gtc acc gcc ctc gac ggc agc gcc gtg gcg ggc gcc cga tga           2061
Met Val Thr Ala Leu Asp Gly Ser Ala Val Ala Gly Ala Arg
        675                 680                 685
```

<210> SEQ ID NO 2
<211> LENGTH: 686
<212> TYPE: PRT
<213> ORGANISM: Streptomyces venezuelae

<400> SEQUENCE: 2

```
Met Arg Thr Leu Leu Ile Asp Asn Tyr Asp Ser Phe Thr His Asn Leu
 1               5                  10                  15

Phe Gln Tyr Ile Gly Glu Ala Thr Gly Gln Pro Pro Val Val Val Pro
             20                  25                  30

Asn Asp Ala Asp Trp Ser Arg Leu Pro Val Glu Asp Phe Asp Ala Ile
         35                  40                  45

Val Val Ser Pro Gly Pro Gly Ser Pro Asp Arg Glu Arg Asp Phe Gly
     50                  55                  60

Ile Ser Arg Arg Ala Ile Thr Asp Ser Gly Leu Pro Val Leu Gly Val
 65                  70                  75                  80

Cys Leu Gly His Gln Gly Ile Ala Gln Leu Phe Gly Gly Thr Val Gly
                 85                  90                  95

Leu Ala Pro Glu Pro Met His Gly Arg Val Ser Glu Val Arg His Thr
            100                 105                 110

Gly Glu Asp Val Phe Arg Gly Leu Pro Ser Pro Phe Thr Ala Val Arg
        115                 120                 125

Tyr His Ser Leu Ala Ala Thr Asp Leu Pro Asp Glu Leu Glu Pro Leu
    130                 135                 140

Ala Trp Ser Asp Asp Gly Val Val Met Gly Leu Arg His Arg Glu Lys
145                 150                 155                 160

Pro Leu Trp Gly Val Gln Phe His Pro Glu Ser Ile Gly Ser Asp Phe
                165                 170                 175

Gly Arg Glu Ile Met Ala Asn Phe Arg Asp Leu Ala Leu Ala His His
            180                 185                 190

Arg Ala Arg Arg His Gly Ala Asp Ser Pro Tyr Glu Leu His Val Arg
        195                 200                 205

Arg Val Asp Val Leu Pro Asp Ala Glu Val Arg Arg Gly Cys Leu
    210                 215                 220

Pro Gly Glu Gly Thr Thr Phe Trp Leu Asp Ser Ser Val Leu Glu
225                 230                 235                 240

Gly Ala Ser Arg Phe Ser Phe Leu Gly Asp Asp Arg Gly Pro Leu Ala
                245                 250                 255

Glu Tyr Leu Thr Tyr Arg Val Ala Asp Gly Val Val Ser Val Arg Gly
            260                 265                 270

Ser Asp Gly Thr Thr Thr Arg Thr Arg Arg Pro Phe Phe Asn Tyr Leu
        275                 280                 285

Glu Glu Gln Leu Glu Arg Arg Arg Val Pro Val Ala Pro Glu Leu Pro
    290                 295                 300

Phe Glu Phe Asn Leu Gly Tyr Val Gly Tyr Leu Gly Tyr Glu Leu Lys
305                 310                 315                 320

Ala Glu Thr Thr Gly Asp Pro Ala His Arg Ser Pro His Pro Asp Ala
                325                 330                 335

Ala Phe Leu Phe Ala Asp Arg Ala Ile Ala Leu Asp His Gln Glu Gly
            340                 345                 350

Cys Cys Tyr Leu Leu Ala Leu Asp Arg Arg Gly His Asp Asp Gly Ala
        355                 360                 365

Arg Ala Trp Leu Arg Glu Thr Ala Glu Thr Leu Thr Gly Leu Ala Val
```

-continued

```
                            370                375                380
Arg Ala Pro Ala Glu Pro Thr Pro Ala Met Val Phe Gly Ile Pro Glu
385                    390                395                400

Ala Ala Ala Gly Phe Gly Pro Leu Ala Arg Ala Arg His Asp Lys Asp
                405                410                415

Ala Tyr Leu Lys Arg Ile Asp Glu Cys Leu Lys Glu Ile Arg Asn Gly
            420                425                430

Glu Ser Tyr Glu Ile Cys Leu Thr Asn Met Val Thr Ala Pro Thr Glu
        435                440                445

Ala Thr Ala Leu Pro Leu Tyr Ser Ala Leu Arg Ala Ile Ser Pro Val
450                455                460

Pro Tyr Gly Ala Leu Leu Glu Phe Pro Glu Leu Ser Val Leu Ser Ala
465                470                475                480

Ser Pro Glu Arg Phe Leu Thr Ile Gly Ala Asp Gly Val Glu Ser
                485                490                495

Lys Pro Ile Lys Gly Thr Arg Pro Arg Gly Thr Ala Glu Glu Asp
            500                505                510

Glu Arg Leu Arg Ala Asp Leu Ala Gly Arg Glu Lys Asp Arg Ala Glu
        515                520                525

Asn Leu Met Ile Val Asp Leu Val Arg Asn Asp Leu Asn Ser Val Cys
530                535                540

Ala Ile Gly Ser Val His Val Pro Arg Leu Phe Glu Val Glu Thr Tyr
545                550                555                560

Ala Pro Val His Gln Leu Val Ser Thr Ile Arg Gly Arg Leu Arg Pro
                565                570                575

Gly Thr Ser Thr Ala Ala Cys Val Arg Ala Ala Phe Pro Gly Gly Ser
            580                585                590

Met Thr Gly Ala Pro Lys Lys Arg Thr Met Glu Ile Ile Asp Arg Leu
        595                600                605

Glu Glu Gly Pro Arg Gly Val Tyr Ser Gly Ala Leu Gly Trp Phe Ala
        610                615                620

Leu Ser Gly Ala Ala Asp Leu Ser Ile Val Ile Arg Thr Ile Val Leu
625                630                635                640

Ala Asp Gly Gln Ala Glu Phe Gly Val Gly Gly Ala Ile Val Ser Leu
                645                650                655

Ser Asp Gln Glu Glu Glu Phe Thr Glu Thr Val Val Lys Ala Arg Ala
            660                665                670

Met Val Thr Ala Leu Asp Gly Ser Ala Val Ala Gly Ala Arg
        675                680                685
```

<210> SEQ ID NO 3
<211> LENGTH: 312
<212> TYPE: DNA
<213> ORGANISM: Streptomyces venezuelae
<220> FEATURE:
<221> NAME/KEY: CDS
<222> LOCATION: (1)..(309)

<400> SEQUENCE: 3

```
atg acc gag cag aac gag ctg cag cgg ctg cgc gcg gag ctc gac gcc    48
Met Thr Glu Gln Asn Glu Leu Gln Arg Leu Arg Ala Glu Leu Asp Ala
  1               5                  10                  15 ctc gac ggg acg ctc ctg gac acg gtg cgg cgc cgc atc gac ctc ggt    96
Leu Asp Gly Thr Leu Leu Asp Thr Val Arg Arg Arg Ile Asp Leu Gly
             20                  25                  30 gtc cgc atc gcg cgg tac aag tcc cgg cac ggc gtc ccg atg atg cag   144
```

-continued

```
                Val Arg Ile Ala Arg Tyr Lys Ser Arg His Gly Val Pro Met Met Gln
                         35                  40                  45 ccc ggc cgg gtc agc ctg gtc aag gac agg gcc gcc cgc tac gcc gcc                192
Pro Gly Arg Val Ser Leu Val Lys Asp Arg Ala Ala Arg Tyr Ala Ala
 50                  55                  60 gac cac ggc ctc gac gaa tcg ttc ctg gtg aac ctc tac gac gtg atc                240
Asp His Gly Leu Asp Glu Ser Phe Leu Val Asn Leu Tyr Asp Val Ile
 65                  70                  75                  80 atc acg gag atg tgc cgc gtc gag gac ctg gtg atg agc cgg gag agc                288
Ile Thr Glu Met Cys Arg Val Glu Asp Leu Val Met Ser Arg Glu Ser
                     85                  90                  95 ctg acg gcc gag gac cgg cgg tga                                                312
Leu Thr Ala Glu Asp Arg Arg
                100
```

<210> SEQ ID NO 4
<211> LENGTH: 103
<212> TYPE: PRT
<213> ORGANISM: Streptomyces venezuelae

<400> SEQUENCE: 4

```
Met Thr Glu Gln Asn Glu Leu Gln Arg Leu Arg Ala Glu Leu Asp Ala
 1               5                  10                  15

Leu Asp Gly Thr Leu Leu Asp Thr Val Arg Arg Arg Ile Asp Leu Gly
                20                  25                  30

Val Arg Ile Ala Arg Tyr Lys Ser Arg His Gly Val Pro Met Met Gln
         35                  40                  45

Pro Gly Arg Val Ser Leu Val Lys Asp Arg Ala Ala Arg Tyr Ala Ala
 50                  55                  60

Asp His Gly Leu Asp Glu Ser Phe Leu Val Asn Leu Tyr Asp Val Ile
 65                  70                  75                  80

Ile Thr Glu Met Cys Arg Val Glu Asp Leu Val Met Ser Arg Glu Ser
                 85                  90                  95

Leu Thr Ala Glu Asp Arg Arg
                100
```

<210> SEQ ID NO 5
<211> LENGTH: 969
<212> TYPE: DNA
<213> ORGANISM: Streptomyces venezuelae
<220> FEATURE:
<221> NAME/KEY: CDS
<222> LOCATION: (1)..(966)

<400> SEQUENCE: 5

```
atg agc ggc ttc ccc cgc agc gtc gtc gtc ggc ggc agc ggg gcg gtg         48
Met Ser Gly Phe Pro Arg Ser Val Val Val Gly Gly Ser Gly Ala Val
 1               5                  10                  15 ggc ggc atg ttc gcc ggg ctg ctg cgg gag gcg ggc agc cgc acg ctc         96
Gly Gly Met Phe Ala Gly Leu Leu Arg Glu Ala Gly Ser Arg Thr Leu
                20                  25                  30 gtc gtc gac ctc gta ccg ccg ccg gga cgg ccg gac gcc tgc ctg gtg        144
Val Val Asp Leu Val Pro Pro Pro Gly Arg Pro Asp Ala Cys Leu Val
         35                  40                  45 ggc gac gtc acc gcg ccg ggg ccc gaa ctc gcg gcc gcc ctc cgg gac        192
Gly Asp Val Thr Ala Pro Gly Pro Glu Leu Ala Ala Ala Leu Arg Asp
 50                  55                  60 gcg gac ctc gtc ctg ctc gcc gta cac gag gac gtg gcc ctc aag gcc        240
Ala Asp Leu Val Leu Leu Ala Val His Glu Asp Val Ala Leu Lys Ala
 65                  70                  75                  80
```

```
gtg gcg ccc gtg acc cgg ctc atg cgg ccg ggc gcg ctg ctc gcc gac     288
Val Ala Pro Val Thr Arg Leu Met Arg Pro Gly Ala Leu Leu Ala Asp
             85                  90                  95 acc ctg tcc gtc cgg acg ggc atg gcc gcg gag ctc gcg gcc cac gcc     336
Thr Leu Ser Val Arg Thr Gly Met Ala Ala Glu Leu Ala Ala His Ala
            100                 105                 110 ccc ggc gtc cag cac gtg ggc ctc aac ccg atg ttc gcc ccc gcc gcc     384
Pro Gly Val Gln His Val Gly Leu Asn Pro Met Phe Ala Pro Ala Ala
        115                 120                 125 ggc atg acc ggc cga ccc gtg gcc gcc gtg gtc acc agg gac ggg ccg     432
Gly Met Thr Gly Arg Pro Val Ala Ala Val Val Thr Arg Asp Gly Pro
    130                 135                 140 ggc gtc acg gcc ctg ctg cgg ctc gtc gag ggc ggc ggc agg ccc         480
Gly Val Thr Ala Leu Leu Arg Leu Val Glu Gly Gly Gly Arg Pro
145                 150                 155                 160 gta cgg ctc acg gcg gag gag cac gac cgg acg acg gcg gcc acc cag     528
Val Arg Leu Thr Ala Glu Glu His Asp Arg Thr Thr Ala Ala Thr Gln
                165                 170                 175 gcc ctg acg cac gcc gtg ctc ctc tcc ttc ggg ctc gcc ctc gcc cgc     576
Ala Leu Thr His Ala Val Leu Leu Ser Phe Gly Leu Ala Leu Ala Arg
            180                 185                 190 ctc ggc gtc gac gtc cgg gcc ctg gcg gcg acg gca ccg ccg ccc cac     624
Leu Gly Val Asp Val Arg Ala Leu Ala Ala Thr Ala Pro Pro Pro His
        195                 200                 205 cag gtg ctg ctc gcc ctc ctg gcc cgt gtg ctc ggc ggc agc ccc gag     672
Gln Val Leu Leu Ala Leu Leu Ala Arg Val Leu Gly Gly Ser Pro Glu
    210                 215                 220 gtg tac ggg gac atc cag cgg tcc aac ccc cgg gcg gcg tcc gcg cgc     720
Val Tyr Gly Asp Ile Gln Arg Ser Asn Pro Arg Ala Ala Ser Ala Arg
225                 230                 235                 240 cgg gcg ctc gcc gag gcc ctg cgc tcc ttc gcc gcg ctg gtc ggc gac     768
Arg Ala Leu Ala Glu Ala Leu Arg Ser Phe Ala Ala Leu Val Gly Asp
                245                 250                 255 gac ccg gac cgt gcc gac gcc ccc ggg cgc gcc gac gcc ccc ggc cat     816
Asp Pro Asp Arg Ala Asp Ala Pro Gly Arg Ala Asp Ala Pro Gly His
            260                 265                 270 ccc ggg gga tgc gac ggc gcc ggg aac ctc gac ggc gtc ttc ggg gaa     864
Pro Gly Gly Cys Asp Gly Ala Gly Asn Leu Asp Gly Val Phe Gly Glu
        275                 280                 285 ctc cgc cgg ctc atg gga ccg gag ctc gcg gcg ggc cag gac cac tgc     912
Leu Arg Arg Leu Met Gly Pro Glu Leu Ala Ala Gly Gln Asp His Cys
    290                 295                 300 cag gag ctg ttc cgc acc ctc cac cgc acc gac gac gaa ggc gag aag     960
Gln Glu Leu Phe Arg Thr Leu His Arg Thr Asp Asp Glu Gly Glu Lys
305                 310                 315                 320 gac cga tga                                                          969
Asp Arg <210> SEQ ID NO 6
<211> LENGTH: 322
<212> TYPE: PRT
<213> ORGANISM: Streptomyces venezuelae

<400> SEQUENCE: 6

Met Ser Gly Phe Pro Arg Ser Val Val Gly Gly Ser Gly Ala Val
  1               5                  10                  15

Gly Gly Met Phe Ala Gly Leu Leu Arg Glu Ala Gly Ser Arg Thr Leu
             20                  25                  30

Val Val Asp Leu Val Pro Pro Gly Arg Pro Asp Ala Cys Leu Val
         35                  40                  45
```

```
Gly Asp Val Thr Ala Pro Gly Pro Glu Leu Ala Ala Ala Leu Arg Asp
 50                  55                  60

Ala Asp Leu Val Leu Leu Ala Val His Glu Asp Val Ala Leu Lys Ala
 65                  70                  75                  80

Val Ala Pro Val Thr Arg Leu Met Arg Pro Gly Ala Leu Leu Ala Asp
                 85                  90                  95

Thr Leu Ser Val Arg Thr Gly Met Ala Ala Glu Leu Ala Ala His Ala
             100                 105                 110

Pro Gly Val Gln His Val Gly Leu Asn Pro Met Phe Ala Pro Ala Ala
         115                 120                 125

Gly Met Thr Gly Arg Pro Val Ala Val Val Thr Arg Asp Gly Pro
130                 135                 140

Gly Val Thr Ala Leu Leu Arg Leu Val Glu Gly Gly Gly Arg Pro
145                 150                 155                 160

Val Arg Leu Thr Ala Glu Glu His Asp Arg Thr Thr Ala Ala Thr Gln
                165                 170                 175

Ala Leu Thr His Ala Val Leu Leu Ser Phe Gly Leu Ala Leu Ala Arg
            180                 185                 190

Leu Gly Val Asp Val Arg Ala Leu Ala Ala Thr Ala Pro Pro His
        195                 200                 205

Gln Val Leu Leu Ala Leu Leu Ala Arg Val Leu Gly Gly Ser Pro Glu
    210                 215                 220

Val Tyr Gly Asp Ile Gln Arg Ser Asn Pro Arg Ala Ala Ser Ala Arg
225                 230                 235                 240

Arg Ala Leu Ala Glu Ala Leu Arg Ser Phe Ala Ala Leu Val Gly Asp
                245                 250                 255

Asp Pro Asp Arg Ala Asp Ala Pro Gly Arg Ala Asp Ala Pro Gly His
            260                 265                 270

Pro Gly Gly Cys Asp Gly Ala Gly Asn Leu Asp Gly Val Phe Gly Glu
        275                 280                 285

Leu Arg Arg Leu Met Gly Pro Glu Leu Ala Ala Gly Gln Asp His Cys
290                 295                 300

Gln Glu Leu Phe Arg Thr Leu His Arg Thr Asp Asp Glu Gly Glu Lys
305                 310                 315                 320

Asp Arg

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:PCR primer
      for the pabAB gene

<400> SEQUENCE: 7 gggggggatcc tatgcgcacg cttctgatcg ac                              32

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:PCR primer
      for the pabAB gene

<400> SEQUENCE: 8 gggggggatcc tcatcgggcg cccgccactg cg                              32
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:PCR primer
      for the papA gene

<400> SEQUENCE: 9
ggtgatcata tgcgcacgct tctgatcgac                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:PCR primer
      for the papA gene

<400> SEQUENCE: 10
ggtgatcatc atcgggcgcc cgccactgcg                                    30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:PCR primer
      for the papB gene

<400> SEQUENCE: 11
gcggatccat atgaccgagc agaacgagct g                                  31

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:PCR primer
      for the papB gene

<400> SEQUENCE: 12
gcggatcctc accgccggtc ctcggc                                        26

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:PCR primer
      for the papC gene

<400> SEQUENCE: 13
gcggatccat atgagcggct tcccccgca                                     29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:PCR primer
      for the papC gene

<400> SEQUENCE: 14
gcggatcctc atcggtcctt ctcgccttc                                     29

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 15
ctcaaaccag gaactctttc                                              20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 16
gacatgtgga aaccacattt tg                                           22

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 17
ggggaattcg tgggtggtga tatcatggc                                    29

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 18
gggggatcct tgatgggttt tggg                                         24

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 19
gggggatcct aaactcccat ctatagc                                      27

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:PCR primer
      for the Abp1 gene

<400> SEQUENCE: 20
gggtctagac gactcattgc agtgagtgg                                    29

-continued

```
<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence:primer for
      site-directed mutagenesis

<400> SEQUENCE: 21
gatcagaagc gtgcgcattg ttaggttgat tgatgggttt tgggaattg            49

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence:primer for
      site-directed mutagenesis

<400> SEQUENCE: 22
ctcgttctgc tcggtcattg ttaggttgat tgatgggttt tgggaattg            49

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence:primer for
      site-directed mutagenesis

<400> SEQUENCE: 23
cgggggaagc cgctcattgt taggttgatt gatgggtttt gggaattg             48
```

TRANSFORMANT PRODUCING SECONDARY METABOLITE MODIFIED WITH FUNCTIONAL GROUP AND NOVEL BIOSYNTHESIS GENES

This application is a 371 of PCT/JP00/06783 filed Sep. 29, 2000, which claims the foreign priority of Japan 11/276314 filed Sep. 29, 1999.

BACKGROUND OF THE INVENTION

1. Field of the Invention

The present invention relates to transformants producing secondary metabolites modified by functional groups, more specifically, to transformants producing secondary metabolites in which a benzene ring is modified at the para-position with a functional group containing a nitrogen atom. Furthermore, the present invention relates to novel genes involved in a biosynthetic pathway from chorismic acid to p-aminophenylpyruvic acid.

2. Description of the Related Art

Since organisms produce a number of various kinds of secondary metabolites having biological activity, research for utilizing these metabolites for drugs for humans and animals, agricultural chemicals, and the like has been actively carried out. However, secondary metabolites from organisms can rarely be utilized for practical use as they are, and accordingly they are generally modified with various functional groups to optimize their biological activity. A modification with a functional group containing a nitrogen atom, such as a nitro group and amino group, is one of the most important modifications.

Chemical methods are available for modifying a certain substance with a nitro group. However, introduction of a nitro group into a benzene ring specifically at the para-position using a chemical method is extremely difficult, and its yield is very low. Furthermore, when a substance to be modified with a nitro group is as complex as a secondary metabolite from an organism, it is even more difficult to specifically modify a benzene ring at the para-position with a nitro group.

On the other hand, methods of introducing an amino group are generally classified into two groups, i.e., enzymatic methods and chemical methods. In enzymatic methods, an enzyme called aminotransferase (EC 2.6.1 group) is used. However, substances which can be a substrate for the aminotransferase are limited, and no enzyme has been known to directly transfer an amino group to a benzene ring. Therefore, only chemical methods have been available for modification of a benzene ring with an amino group.

However, in chemical procedure, it is necessary to first modify a benzene ring with a nitro group and then to reduce this nitro group into an amino group. Since the nitration reaction in the first step is very difficult, introduction of the amino group into the benzene ring by chemical methods is extremely difficult. Accordingly, development of a method of modifying a benzene ring specifically at the para-position with a nitro group or an amino group has been strongly needed.

SUMMARY OF THE INVENTION

An objective of the present invention is to provide a transformant modified so as to produce a secondary metabolite in which a benzene ring of the secondary product is modified at the para-position with a functional group containing a nitrogen atom, and a method of producing the modified secondary metabolite with ease and at low costs.

The present inventors have successfully obtained a transformant that produces a substance PF1022 in which a benzene ring is modified at the para-position with an amino group by transforming a microorganism producing the substance PF1022 containing a benzene ring skeleton with a DNA containing a gene involved in a biosynthetic pathway from chorismic acid to p-aminophenylpyruvic acid.

A transformant according to the present invention is a transformant of an organism producing a secondary metabolite having a benzene ring skeleton that is not substituted with a functional group containing a nitrogen atom at the para-position, wherein the transformant is transformed by introducing a gene involved in a biosynthetic pathway from chorismic acid to p-aminophenylpyruvic acid (hereinafter refer to as "biosynthesis gene") so that the transformant produces a secondary metabolite having a benzene ring skeleton substituted at the para-position with a functional group containing a nitrogen atom.

A method according to the present invention is a method for producing a secondary metabolite having a benzene ring skeleton substituted at the para-position with a functional group containing a nitrogen atom, which comprises the steps of culturing the above-mentioned transformant and collecting the secondary metabolite having a benzene ring skeleton substituted at the para-position with a functional group containing a nitrogen atom.

Another objective of the present invention is to provide a novel gene involved in the biosynthetic pathway from chorismic acid to p-aminophenylpyruvic acid.

Novel genes according to the present invention are a gene encoding the amino acid sequence of SEQ ID NO: 2 or a modified sequence of SEQ ID NO: 2 having 4-amino-4-deoxychorismic acid synthase activity; a gene encoding the amino acid sequence of SEQ ID NO: 4 or a modified sequence of SEQ ID NO: 4 having 4-amino-4-deoxychorismic acid mutase activity; and a gene encoding the amino acid sequence of SEQ ID NO: 6 or a modified sequence of SEQ ID NO: 6 having 4-amino-4-deoxyprephenic acid dehydrogenase activity.

BRIEF DESCRIPTION OF THE DRAWINGS

FIG. 4 shows the construction of plasmid pTrc-papB.

FIG. 6 shows the construction of plasmid pET-papC1.

FIG. 12 shows the construction of plasmid pPF260-C3.

DESCRIPTION OF THE PREFERRED EMBODIMENTS

Deposition of Microorganisms

Figure 1:
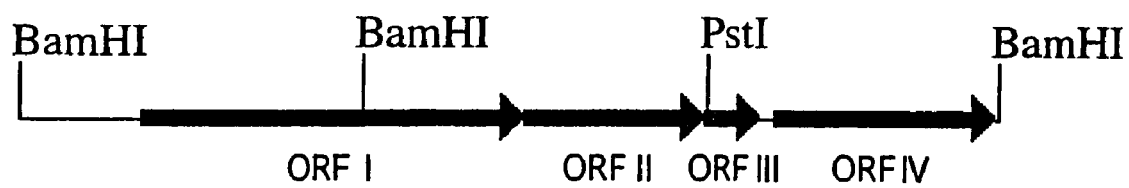
FIG. 1 shows the restriction map of a DNA fragment isolated from *Streptomyces venezuelae* and the position of open reading frames thereon.

The strain PF1022 described in Example 5 was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Jan. 24, 1989. The accession number is FERM BP-2671.

The transformant 55-65 of *Mycelia sterilia* was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Sep. 17, 1999. The accession number is FERM BP-7255.

*Escherichia coli* (JM109) transformed with plasmid pUC118-papA was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Sep. 17, 1999. The accession number is FERM BP-7256.

*Escherichia coli* (JM109) transformed with plasmid pTrc-papB was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Sep. 17, 1999. The accession number is FERM BP-7257.

*Escherichia coli* (JM109) transformed with plasmid pET-papC was deposited with the National Institute of Bioscience and Human-Technology, Agency of Industrial Science and Technology, the Ministry of International Trade and Industry (1-3 Higashi 1-Chome, Tsukuba City, Ibaraki Prefecture, Japan), dated Sep. 17, 1999. The accession number is FERM BP-7258.

Organisms to be Transformed

Organisms to be used in the present invention can be those which produce a secondary metabolite containing a benzene ring skeleton. Examples of preferable organisms include those which produce a secondary metabolite biosynthesized via chorismic acid, in particular, a secondary metabolite synthesized from at least one building block selected from the group consisting of phenylpyruvic acid, p-hydroxyphenylpyruvic acid, phenylalanine, tyrosine, and phenyllactic acid.

Examples of preferable organisms also include those which produce a peptide or a depsipeptide, in particular, a peptide or a depsipeptide synthesized from at least one building block selected from the group consisting of phenylalanine, tyrosine, and phenyllactic acid, as a secondary metabolite.

Such secondary metabolites and microorganisms producing the same include the following.

| Names of Compounds and Microorganisms | |
|---|---|
| Olstatin D | *Bacillus cereus* KY-21, *Nigrosabulum* sp. 28Y1 |
| Nannochelin | *Nannocystis exedens* Nae485 |
| Phosphonophenylalanylarginine 15B1 | *Streptomyces rishiensis* NK-122, *Actinomadura spiculoosospora* K-4 |
| Ahpatinin A | *Streptomyces* sp. WK-142 |
| A-38533 | *Streptomyces* sp. |
| Melanostatin | *Streptomyces clavus* N924-1, *Streptomyces clavifer* N924-2 |
| Aldostatin | *Pseudoeurotium zonatum* M4109 |
| N-Acetyl-L-phenylalanyl-L-phenylalaninol | *Emericellopsis salmosynemata* |
| Bestatin | *Streptomyces olivoverticuli* |
| Estatin A | *Myceliophthora thermophilia* M4323 |
| N-(N-L-Arginyl-D-allo-threonyl)-L-phenylalanine | *Keratinophyton terreum* Tu 534 |
| Streptin P1 | *Streptomyces tanabeensis* |
| WF-10129 | *Doratomyces putredinis* F-214690 |
| Clobamide | *Kobatiella caulivora* |
| SP-Chymostatin B | *Streptomyces nigrescens* WT-27, *Streptomyces libani*, *Streptomyces* sp. GE16457 |
| Antipain | *Streptomyces* sp. KC84-AG13 |
| Milolysine $K_A$ | *Metarrhizium anisopliae* U-47 |
| Tyrostatin | *Kitasatospora* sp. 55, *Streptomyces* sp. SAM-0986 |
| Detoxin | *Streptomyces caespitosus* var. *detoxicus* 7072 $GC_1$, *Streptomyces mobaraensis* |
| Chymostatin | *Streptomyces* sp. |
| Tridecaptin | *Bacillus polymyxa* |
| Alamecycine | *Trichoderma viridis* |
| Trichocerine | *Trichoderma viride* |
| Trichosporin B | *Trichoderma polysporum* |
| Trichodyanine | *Trichoderma polysporum*, *Trichoderma harzianum* |
| Samarosporin I | *Emericellopsis microspora*, *Samarospora* sp., *Stibella* sp. |
| Suzukacyline A | *Trichoderma viride* |
| Trichologin | *Trichoderma longibrachiatum* |
| Zervamicin | *Emericellopsis microspora*, *Emericellopsis salmosynnemata* |
| Antianiebin | *Emericellopsis synnematicola*, *Emericellopsis poonesis*, *Cephalosporum pimprina* |
| Gramicidin C | *Bacillus brevis* |
| Ochratoxins | *Aspergillus ochraceus*, *Aspergillus melleus*, *Aspergillus sulphureus*, *Penicillium viridicatum* |
| FR-900261 | *Petriella* sp., *Petriella guttulata* 3161 |
| Chiamydocine | *Diheterospora chlamydosporia* |
| Trapoxin | *Helicoma ambiens* RF-1023 |
| Cyl-1 | *Cylindrocladium scoparium* |
| Cyl-2 | *Cylindrocladium scoparium* |
| Aspercholine | *Aspergillus versicolor* |
| Lotusine | *Zizyphus lotus* |
| Lyciumin | *Lycium chinense* Mill. |
| Avellanin | *Hamigera avellanea*, *Penicillium* sp. PF1119 |
| Cycloasptide | *Aspergillus* sp. NE-45 |
| Bouvardine | *Bouvardia ternifolia*, *Rubia cordifolia* |
| Cycloamanide A | *Amanitia phalloides* |
| Cycloamanide B | *Amanitia phalloides* |
| Heterophyllin A | *Pseudostellarea heterophylla* |
| Polymyxin | *Bacillus polymyxa* |
| Octapeptin | *Bacillus cirrculans* G493-B6, *Bacillus* sp. JP301 |
| Bu-2470A | *Bacillus circulans* |
| Mucosubtilin | *Bacillus subtilis* |
| Bacillomycin D | *Bacillus subtilis* I-164, *Bacillus subtilis* Sc-3 |
| Iturin A | *Bacillus subtilis* |
| Cyanogicin | *Microcystis aeruginosa* |
| Bacitracin | *Bacillus subtilis*, *Bacillus licheniformis* |
| Gramicidin S | *Bacillus brevis* |
| Antamanide | *Amanitia phalloides* |
| Tyrocidin | *Bacillus brevis* |
| Cortinarine | *Cortinarius speciosissimus* |
| Mycobacillin | *Bacillus subtilis* |
| TL119 | *Bacillus subtilis* |
| Beauverolide | *Beauveria bassiana*, *Isaria* sp. |
| Neoantimycin | *Streptoverticillium orinoci* |
| MK3990 | *Basidiobolus* sp. MK3990 |

-continued

Names of Compounds and Microorganisms

| | |
|---|---|
| Leualacin | *Hapsidospora irregularis* SANK 17182 |
| A54556 | *Streptomyces hawaiiensis* |
| Enopeptin B | *Streptomyces* sp. RK-1051 |
| Beauvaricin | *Beauveria bassiana* |
| Xanthostatin | *Streptomyces spiroverticillatus* |
| Valiapeptin | *Streptomyces citrus* K3619, *Streptomyces flavidovirens* |
| Verginiamycin $S_1$ | *Streptomyces virginiae, Streptomyces Alborectus* |
| Cycloheptamycin | *Streptomyces* sp. |
| WS-9326 | *Streptomyces violaceusniger* 9326 |
| Fusaria fungi cyclodepsipeptide | *Fusarium sporotrichoides, Fusarium roseum, Fusarium tricinctum* |
| FR-900359 | *Ardisia crenata* |
| Verlamellin | *Verticillium lamellicola* MF4683 |
| Didemnin | *Trididermnum solidam* |
| Lipopeptin A | *Streptomyces* sp. AC-69 |
| 20561 | *Aeromonas* sp. |
| Neopeptin | *Streptomyces* sp. K-710 |
| Aureobasidin | *Aureobasidium pullulans* R106 |
| Syringomycin | *Pseudomonas syringae* pv. *Syringae* |
| Plipastatin | *Bacillus cereus* BMG302-fF67 |
| Permetin A | *Bacillus circulans* H913-B4 |
| BMY-28160 | *Bacillus circulans* |
| Polypeptin A | *Bacillus circulans* |
| Brevistin | *Bacillus brevis* |
| Ramoplanin | *Actinoplanes* sp. ATCC33076 |
| Ancovenin | *Streptomyces* sp. A-647P |
| Duramycins | *Streptomyces hachijoensis* var. *takahagiensis* E-312 *Streptoverticillium griseoluteus* 2075, *Streptoverticillium griseoverticillatum* PA-48009 |
| Cinnamycin | *Streptomyces cinnamoneus* |
| Actinoidin | *Nocardia actinoides* SKF-AAJ-193, *Proactinomycetes actinoides* |
| Substance PF1022 | *Mycelia sterilia* |

These substances are described in the Dictionary of Natural Products (Chapman & Hall, 1994).

"Organisms" to be transformed in the present invention include microorganisms such as bacteria, yeasts and fungi, and plants. The plants also include plant cells.

Examples of the functional group containing a nitrogen atom include an amino group and nitro group.

When an organism to be transformed is a microorganism that produces the substance PF1022 represented by the following formula:

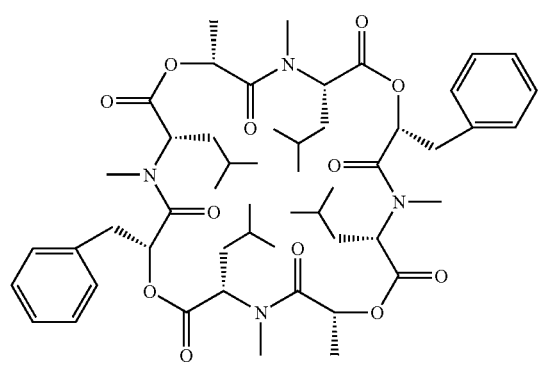

the secondary metabolite produced by the transformant can be the substance PF1022 represented by the following formula, which is modified with an amino group (hereinafter refer to as "substance PF1022 derivative").

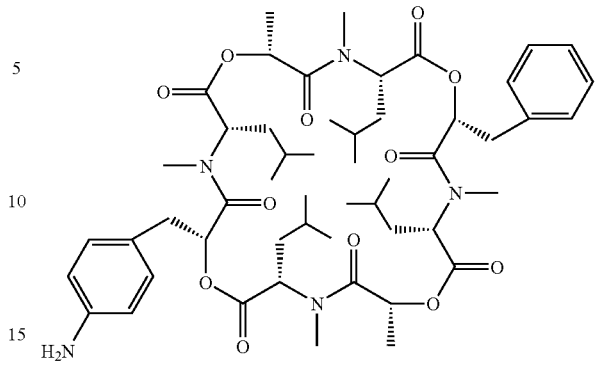

The substance PF1022 [cyclo(D-lactyl-L-N-methylleucyl-D-3-phenyllactyl-L-N-methylleucyl-D-lactyl-L-N-methylleucyl-D-3-phenyllactyl-L-N-methylleucyl)] is a cyclic depsipeptide that is produced by the filamentous fungus strain PF1022 (*Mycelia sterilia*, FERM BP-2671), which belongs to Agonomycetales and has extremely high anthelmintic activity against animal parasitic nematodes (Japanese Patent Application Laid-open Publication No. 35796/1991; Sasaki, T. et al., J. Antibiotics, 45, 692, 1992). Accordingly, the substance PF1022 is useful as an anthelmintic, and also a derivative thereof modified with an amino group is useful as a raw material for synthesizing a highly active derivative of this substance.

The substance PF1022 is synthesized by a substance PF1022-synthesizing enzyme from four molecules of L-leucine, two molecules of D-lactic acid, and two molecules of D-phenyllactic acid. Not restricted to the following, it is thought that (1) p-aminophenylpyruvic acid is produced in a transformant by introducing a gene involved in the biosynthetic pathway from chorismic acid to p-aminophenylpyruvic acid into a substance PF1022-producing microorganism, (2) D-phenyllactic acid dehydrogenase (D-PLDH) acts on the resulting product to produce p-amino-D-phenyllactic acid in the transformant, (3) the substance PF1022-synthesizing enzyme acts on p-amino-D-phenyllactic acid instead of D-phenyllactic acid, and thus (4) the substance PF1022 derivative is produced.

Biosynthesis Genes

Examples of enzymes involved in the biosynthesis from chorismic acid to p-aminophenylpyruvic acid include 4-amino-4-deoxychorismic acid synthase, 4-amino-4-deoxychorismic acid mutase, and 4-amino-4-deoxyprephenic acid dehydrogenase (Blanc, V. et al., Mol. Microbiol., 23, 191–202, 1997). The biosynthetic pathway from chorismic acid to p-aminophenylpyruvic acid can be summarized as follows: 4-Amino-4-deoxychorismic acid synthase acts on chorismic acid to produce 4-amino-4-deoxychorismic acid; 4-amino-4-deoxychorismic acid mutase acts on the resulting 4-amino-4-deoxychorismic acid to produce 4-amino-4-deoxyprephenic acid; and 4-amino-4-deoxyprephenic acid dehydrogenase acts on the resulting 4-amino-4-deoxyprephenic acid to produce p-aminophenylpyruvic acid.

The 4-amino-4-deoxychorismic acid synthase includes an enzyme that acts on chorismic acid to transform it into 4-amino-4-deoxychorismic acid.

The 4-amino-4-deoxychorismic acid synthase is found in a wide variety of organisms as a part of the biosynthesis system from chorismic acid to p-aminobenzoic acid.

p-Aminobenzoic acid is synthesized from chorismic acid in a two-step reaction. The former reaction is catalyzed by 4-amino-4-deoxychorismic acid synthase, and the latter reaction is catalyzed by 4-amino-4-deoxychorismic acid lyase (Green, J. M. and Nichols, B. P., J. Biol. Chem., 266, 12971–12975, 1991).

Reported genes encoding 4-amino-4-deoxychorismic acid synthase include those derived from *Escherichia coli* (Kaplan, J. B. and Nichols, B. P., J. Mol. Biol., 168, 451–468, 1983); Goncharoff, P. and Nichols, B. P., J. Bacteriol., 159, 57–62, 1984), *Bacillus subtilis*(Slock, J. et al., J. Bacteriol., 172, 7211–7226, 1990), *Klebsiella pneumoniae* (Kaplan, J. B. et al., J. Mol. Biol., 183, 327–340, 1985; Goncharoff, P. and Nichols, B. P., Mol. Biol. Evol., 5, 531–548, 1988), *Streptomyces pristinaespiralis* (Blanc, V. et al., Mol. Microbiol., 23, 191–202, 1997), *Streptomyces venezuelae* (Brown, M. P. et al., Microbiology, 142, 1345–1355, 1996), and *Saccharomyces cerevisiae* (Edman, J. C. et al., Yeast, 9, 669–675, 1993), and they can be used. Genes encoding the 4-amino-4-deoxychorismic acid synthase, other than those mentioned above, can also be isolated from organisms having 4-amino-4-deoxychorismic acid synthase activity using standard techniques and used in the present invention.

On the other hand, the 4-amino-4-deoxychorismic acid synthase can be generally divided into two groups: one which is composed of two polypeptides, such as those derived from *Escherichia coli, Bacillus subtilis*, or *Klebsiella pneumoniae*, and the other which is composed of one peptide, such as those from a part of Actinomycetes or *Saccharomyces cerevisiae*. In the present invention, it is preferable to use a gene encoding the 4-amino-4-deoxychorismic acid synthase consisting of one polypeptide since a plurality of genes has to be introduced to a host.

In the present invention, an example of the gene encoding the 4-amino-4-deoxychorismic acid synthase is preferably a gene encoding the amino acid sequence of SEQ ID NO: 2 or a modified sequence of SEQ ID NO:2 having 4-amino-4-deoxychorismic acid synthase activity, more preferably a gene containing the DNA sequence of SEQ ID NO: 1.

In the present invention, "modified sequence" means a sequence having one or more, for example one to several, modifications selected from the group consisting of a substitution, a deletion, an insertion, and an addition.

In the present invention, whether a modified amino acid sequence "has 4-amino-4-deoxychorismic acid synthase activity" or not can be evaluated by allowing the protein comprising said amino acid sequence to act on a substrate and then detecting the reaction product, for example, according to the method described in Example 2.

The 4-amino-4-deoxychorismic acid mutase means an enzyme that acts on 4-amino-4-deoxychorismic acid to transform it into 4-amino-4-deoxyprephenic acid.

The 4-amino-4-deoxyprephenic acid dehydrogenase means an enzyme which acts on 4-amino-4-deoxyprephenic acid to transform it into p-aminophenylpyruvic acid.

A gene encoding 4-amino-4-deoxychorismic acid mutase and a gene encoding 4-amino-4-deoxyprephenic acid dehydrogenase are obtained from organisms that can biosynthesize p-aminophenylpyruvic acid. More specifically, examples of such organisms include *Streptomyces pristinaespiralis* that produces pristinamycin I; *Streptomyces loidensis* that produces vernamycin B; *Corynebacterium hydrocarboclastus* that produce corynecin; and *Streptomyces venezuelae* that produces chloramphenicol. Among these organisms, *Streptomyces pristinaespiralis* can be used in the present invention since genes which presumably encode 4-amino-4-deoxychorismic acid mutase and 4-amino-4-deoxyprephenic acid dehydrogenase have already been isolated and their nucleotide sequences have been determined (V. Blanc et al., Mol. Microbiol., 23, 191–202, 1997).

A number of genes encoding chorismic acid mutase and prephenic acid dehydrogenase have been already isolated from bacteria, yeasts, plants and the like, and these genes can be modified by substituting, deleting or adding appropriate amino acids so as to have 4-amino-4-deoxychorismic acid mutase activity and 4-amino-4-deoxyprephenic acid dehydrogenase activity, based on protein engineering techniques or directed evolution techniques. Thus, the resulting modified genes can also be used in the present invention.

In the present invention, an example of the gene encoding the 4-amino-4-deoxychorismic acid mutase is preferably a gene encoding the amino acid sequence of SEQ ID NO: 4 or a modified sequence of SEQ ID NO:4 having 4-amino-4-deoxychorismic acid mutase activity, more preferably a gene containing the DNA sequence of SEQ ID NO: 3.

In the present invention, whether a modified amino acid sequence "has 4-amino-4-deoxychorismic acid mutase activity" or not can be evaluated by allowing the protein comprising said amino acid sequence to act on a substrate and then detecting the reaction product, for example, according to the method described in Example 3.

In the present invention, an example of the gene encoding the 4-amino-4-deoxyprephenic acid dehydrogenase is preferably a gene encoding the amino acid sequence of SEQ ID NO: 6 or a modified sequence of SEQ ID NO: 6 having 4-amino-4-deoxyprephenic acid dehydrogenase activity, more preferably a gene containing the DNA sequence of SEQ ID NO: 5.

In the present invention, whether a modified amino acid sequence "has 4-amino-4-deoxyprephenic acid dehydrogenase activity" or not can be evaluated by allowing the protein comprising said amino acid sequence to act on a substrate and then detecting the reaction product, for example, according to the method described in Example 4.

Given the amino acid sequences of enzymes involved in the biosynthesis in the present invention, nucleotide sequences encoding the amino acid sequences can be easily determined, and various nucleotide sequences encoding the amino acid sequences depicted in SEQ ID NOs: 2, 4, and 6 can be selected. Accordingly, biosynthesis genes according to the present invention include, in addition to a part or all of the DNA sequences of SEQ ID NOs: 1, 3, and 5, DNA sequences encoding the same amino acid sequences and having degenerate codons, and further include RNA sequences corresponding to these sequences.

Transformants

A transformant of the present invention can be obtained by introducing a DNA molecule, in particular an expression vector, comprising a gene involved in the biosynthesis from chorismic acid to p-aminophenylpyruvic acid into a host, wherein the DNA molecule is replicable and the gene can be expressed.

In the present invention, when a plurality of biosynthesis enzyme genes is introduced into the host, each gene can be contained in either the same or different DNA molecules. Further, when the host is a bacterium, each gene can be designed to be expressed as a polycistronic mRNA so as to be made into a single DNA molecule.

The expression vector to be used in the present invention can be appropriately selected from viruses, plasmids, cosmid vectors, and the like taking the kind of the host cell to be used into consideration. For example, lambda bacteriophages and pBR and pUC plasmids can be used when the host cell is *Escherichia coli*; pUB plasmids can be used for *Bacillus subtilis*; and YEp, YRp, YCp, and YIp plasmid vectors can be used for yeasts.

Among the plasmid vectors to be used, at least one vector preferably contains a selectable marker to select transformants. A drug resistance gene or a gene complementing an auxotrophic mutation can be used as a selectable maker. Preferable examples of the marker genes to be used for each host include an ampicillin resistance gene, a kanamycin resistance gene and a tetracycline gene for bacteria; a tryptophan biosynthesis gene (TRP1), an uracil biosynthesis gene (URA3) and a leucine biosynthesis gene (LEU2) for yeasts; a hygromycin resistance gene, a bialaphos resistance gene, a bleomycin resistance gene and an aureobasidin resistance gene for fungi; and a kanamycin resistance gene and a bialaphos resistance gene for plants.

Furthermore, in an expression vector, regulatory sequences necessary for expression of the individual genes, for example, transcription regulatory signals and translation regulatory signals, such as a promoter, a transcription initiation signal, a ribosome binding site, a translation stop signal, and a transcription stop signal, can operably be linked to the biosynthesis gene. The regulatory sequences can be selected and ligated according to an ordinary method.

For example, promoters such a lactose operon and a tryptophan operon can be used in *Escherichia coli*; promoters of an alcohol dehydrogenase gene, an acid phosphatase gene, a galactose utilization gene, and a glyceraldehyde 3-phosphate dehydrogenase gene can be used in yeasts; promoters such as α-amylase gene, a glucoamylase gene, a cellobiohydrolase gene, a glyceraldehyde 3-phosphate dehydrogenase gene, and an Abp1 gene can be used in fungi; and the CaMV 35SRNA promoter, a CaMV 19SRNA promoter, a noparin synthase gene promoter can be used in plants.

Transformation of an organism can be carried out according to an ordinary method such as the calcium ion method, the lithium ion method, the electroporation method, the PEG method, the *Agrobacterium* method, and the particle gun method, and the method can be selected depending on the organism to be transformed.

In the present invention, a transformant is cultured, and the resultant culture is used to obtain a modified secondary metabolite of interest. The transformant can be cultured also according to an ordinary method by appropriately selecting a medium, culture conditions, and the like.

The medium can be supplemented with a carbon source and nitrogen source that can be anabolized and utilized, respectively, by the transformant of the present invention, various vitamins, various amino acids such as glutamic acid and asparagine, trace nutrients such as nucleotides, and selective agents such as antibiotics. Further, organic and inorganic substances that help the growth of the transformant of the present invention or promote the production of the secondary metabolite of interest can be appropriately added. Further, if necessary, a synthetic medium or complex medium which appropriately contains other nutrients can be used.

Any kind of carbon source and nitrogen source can be used in the medium as long as they can be utilized by the transformant of the present invention. As the anabolizable carbon source, for example, various carbohydrates, such as sucrose, glucose, starch, sucrose, glycerol, fructose, maltose, mannitol, xylose, galactose, ribose, dextrin, animal and plant oils and the like, or hydrolysates thereof, can be used. The preferable concentration generally is from 0.1% to 5% of the medium.

As the utilizable nitrogen source, for example, animal or plant components, or exudates or extracts thereof, such as peptone, meat extract, corn steep liquor, and defatted soybean powder, organic acid ammonium salts such as succinic acid ammonium salts and tartaric acid ammonium salts, urea, and other various inorganic or organic nitrogen-containing compounds can be used.

Further, as inorganic salts, for example, those which can produce sodium, potassium, calcium, magnesium, cobalt, chlorine, phosphoric acid, sulfuric acid, and other ions can be appropriately used.

Of course, any medium which contains other components, such as cells, exudates or extracts of microorganisms such as yeasts, and fine plant powders, can be appropriately used as long as they don't interfere with the growth of the transformant and the production and accumulation of the secondary metabolite of interest. When a mutant strain having a nutritional requirement is cultured, a substance to satisfy its nutritional requirement is added to the medium. However, this kind of nutrient may not necessarily be added when a medium containing natural substances is used.

The pH of the medium is, for example, about 6 to 8. Incubation can be carried out by a shaking culture method under an aerobic condition, an agitation culture method with aeration, or an aerobic submerged culture method. An appropriate incubation temperature is 15° C. to 40° C., generally about 26° C. to 37° C. Production of the secondary metabolite of interest depends on a medium, culture conditions, or a host used. However, the maximum accumulation can generally be attained in 2 to 25 days by any culture method. The incubation is terminated when the amount of the secondary metabolite of interest in the medium reaches its peak, and the target substance is isolated from the culture and then purified.

Needless to say, the culture conditions such as the medium component, medium fluidity, incubation temperature, agitation speed and aeration rate can be appropriately selected and controlled depending on the transformant to be used and the exterior conditions so as to obtain preferable results. If foaming occurs in a liquid medium, a defoaming agent such as silicone oil, vegetable oils, mineral oils, and surfactants can be appropriately used. The secondary metabolite of interest accumulated in the culture thus obtained is contained in the cells of the transformant of the present invention and the culture filtrate. Accordingly, it is possible to recover the secondary metabolite of interest from both culture filtrate and transformant cells by separating the culture into each fraction by centrifugation.

The secondary metabolite of interest can be recovered from the culture filtrate according to an ordinary method. Procedures for recovering the secondary metabolite of interest from the culture can be carried out singly, in combination in a certain order, or repeatedly. For example, extraction filtration, centrifugation, salting out, concentration, drying, freezing, adsorption, detaching, means for separation based on the difference in solubility in various solvents, such as precipitation, crystallization, recrystallization, reverse solution, counter-current distribution, and chromatography can be used.

Further, the secondary metabolite of interest can be obtained from the culture inside the cells of the transformant of the present invention. For example, extraction from the culture (e.g., smashing and pressure disruption), recovery (e.g., filtration and centrifugation), and purification (e.g., salting out and solvent precipitation) can be carried out using an ordinary method.

The crude substance obtained can be purified according to an ordinary method, for example, by column chromatography using a carrier such as silica gel and alumina or reverse-phase chromatography using an ODS carrier. A pure secondary metabolite of interest can be obtained from the culture of the transformant of the present invention using the above-mentioned methods, either singly or in appropriate combination.

Transformants Producing Substance PF1022 Derivative

A preferable embodiment of the present invention provides a transformant of a substance PF1022-producing microorganism into which a gene involved in the biosynthetic pathway from chorismic acid to p-aminophenylpyruvic acid (biosynthesis gene) is introduced.

This transformant can produce a substance PF1022 derivative.

The substance PF1022-producing microorganism to be transformed can be *Mycelia sterilia*, preferably the strain deposited with the National Institute of Bioscience and Human-Technology under an accession number of FERM BP-2671.

The biosynthesis gene can comprise a gene encoding 4-amino-4-deoxychorismic acid synthase, a gene encoding 4-amino-4-deoxychorismic acid mutase, and a gene encoding 4-amino-4-deoxyprephenic acid dehydrogenase. The gene encoding 4-amino-4-deoxychorismic acid synthase can preferably be a gene encoding the amino acid sequence of SEQ ID NO: 2 or a modified sequence of SEQ ID NO: 2 having 4-amino-4-deoxychorismic acid synthase activity. The gene encoding 4-amino-4-deoxychorismic acid mutase can preferably be a gene encoding the amino acid sequence of SEQ ID NO: 4 or a modified sequence of SEQ ID NO: 4 having 4-amino-4-deoxychorismic acid mutase activity. The gene encoding 4-amino-4-deoxyprephenic acid dehydrogenase can preferably be a gene encoding the amino acid sequence of SEQ ID NO: 6 or a modified sequence of SEQ ID NO: 6 having 4-amino-4-deoxyprephenic acid dehydrogenase activity.

An expression vector to be used for transformation is preferably an expression vector in which the biosynthesis gene is operably linked to a regulatory sequence (e.g., promoter, terminator) which functions in a substance PF1022-producing microorganism, most preferably an expression vector in which the biosynthesis gene is operably linked to a regulatory sequence which functions in the strain PF1022 (*Mycelia sterilia*, FERM BP-2671).

The transformant can be the transformant 55-65 strain deposited with the National Institute of Bioscience and Human-Technology under an accession number of FERM BP-7255.

Another embodiment of the present invention provides a method of producing a substance PF1022 derivative, which comprises the steps of culturing a transformant of a substance PF1022-producing microorganism and recovering the substance PF1022 derivative from the culture.

EXAMPLE

The present invention is further illustrated by the following examples that are not intended as a limitation.

Example 1

Isolation of a Gene Encoding
4-amino-4-deoxychorismic Acid Synthase, a Gene
Encoding 4-amino-4-deoxychorismic Acid Mutase,
and a Gene Encoding 4-amino-4-deoxyprephenic
Acid Dehydrogenase from *Streptomyces venezuelae*

(1) Preparation of Probe DNA Fragment

A 50 ml portion of a liquid medium (2% soluble starch, 1% polypeptone, 0.3% meat extract, 0.05% potassium dihydrogenphosphate, pH 7.0) was prepared in a 250-ml Erlenmeyer flask. The ISP5230 strain and 140-5 strain of *Streptomyces venezuelae* were each inoculated into this medium and cultured at 28° C. for 24 hours. After culturing, the cells were harvested from the culture by centrifugation, and the chromosome DNA was prepared from these cells by the method described in Genetic Manipulation of *Streptomyces*, A Laboratory Manual (D. A. Hopwood et al., The John Innes Foundation, 1985).

Next, PCR was carried out using the above-mentioned chromosomal DNA of the *Streptmyces venezuelae* strain ISP5230 as a template and oligonucleotides of SEQ ID NO: 7 and SEQ ID NO: 8 as primers. The PCR was carried out with a TaKaRa LA PCR™ kit Ver. 2.1 (Takara Shuzo Co., Ltd.) and Gene Amp PCR System 2400 (Perkin-Elmer). A reaction solution containing 1 μl of the chromosomal DNA (equivalent to 0.62 μg), 5 μl of 10-fold concentrated reaction buffer attached to the kit, 8 μl of a 2.5 mM dNTP solution, 0.5 μl each of the above-mentioned primers prepared at a concentration of 100 pmol/μl, 5 μl of dimethyl sulfoxide (Wako Pure Chemical Industries, Ltd.), 0.5 μl of TaKaRa LA-Taq (2.5 U), and 29.5 μl of sterile water was made up into a total volume of 50 μl. The reaction was carried out by repeating incubation of 25 cycles of one minute at 94° C., one minute at 50° C. and 3 minutes at 72° C., after pretreatment at 94° C. for 10 minutes. After the reaction, a portion of the reaction solution was subjected to agarose gel electrophoresis to confirm that a DNA fragment of approximately 2 kbp was specifically amplified. Then, the remaining reaction solution was extracted with phenol:chloroform:isoamyl alcohol (25:24:1) and precipitated with ethanol. The precipitate was redissolved in sterile water, and the resulting solution (60 μl) was digested with restriction enzyme BamHI, after which agarose gel electrophoresis was carried out, and a band of approximately 2 kbp was isolated according to an ordinary method to recover a DNA fragment.

This DNA fragment was cloned into the BamHI site of plasmid pTrcHis B (Invitrogen). Since the restriction map of the inserted fragment of the resulting plasmid was identical to that of pabAB gene (U21728) reported by Brown et al. (M. P. Brown et al., Microbiology, 142, 1345–1355, 1996), the pabAB gene was considered to be cloned, and the plasmid was named pTH-PAB. The plasmid pTH-PAB was digested with restriction enzyme BamHI, agarose gel electrophoresis was carried out, and an insertion fragment was isolated and recovered to be used as a probe for the screening of a chromosomal DNA library described below.

(2) Screening of Chromosomal DNA Library and Isolation of Genes

About 10 μl of the chromosomal DNA of the *Streptomyces venezuelae* 140-5 strain was partly digested with restriction enzyme Sau3AI, after which agarose gel electrophoresis was carried out to isolate and recover DNA fragments of from 10 kbp to 20 kbp.

About 0.5 μg of the DNA fragments of from 10 kbp to 20 kbp thus recovered and 1 μl of λDASH II previously double-digested with restriction enzymes BamHI and XhoI were ligated with T4 DNA ligase and then packaged in vitro using a Gigapack III packaging extract (Stratagene) to construct a chromosomal DNA library. Plaques were formed by infecting *Escherichia coli* XLI-Blue MRA with this DNA library.

Plaque hybridization was carried out using the DNA fragment of approximately 2 kbp isolated in (1) as a probe and an ECL Direct DNA/RNA Labeling Detection System (Amersham Pharmacia Biotech) to screen about 24000 plaques. Among positive clones thus obtained, ten clones were subjected to a secondary screening, and the resulting positive clones were purified to prepare phage DNAs.

These phage DNAs were digested with restriction enzyme BamHI, and Southern analysis was carried out, which revealed that the probe was hybridized with two kinds of DNA fragments, i.e., fragments of approximately 1.8 kbp and approximately 3.4 kbp. Further, restriction map analysis of the phage DNAs revealed that these two kinds of DNA fragments were adjoining on the chromosomal DNA.

Next, the entire nucleotide sequences of these two kinds of DNA fragments were determined using a fluorescent DNA sequencer ABI PRISM 377 (Perkin-Elmer). As a result of the subsequent open-reading-frame (ORF) search, ORFs I–IV were found as shown in FIG. 1. The amino acid sequences deduced from each of the ORFs were searched for homology with known amino acid sequences using database, which revealed that ORF I was homologous to p-aminobenzoic acid-synthesizing enzyme, ORF II was homologous to prephenic acid dehydrogenase, and ORF III was homologous to chorismic acid mutase. Genes of ORF I, II and III were then named papA, papC and papB, respectively. The amino acid sequence encoded by papA and the nucleotide sequence of papA are each shown in SEQ ID NO: 2 and SEQ ID NO: 1; the amino acid sequence encoded by papB and the nucleotide sequence of papB are each shown in SEQ ID NO: 4 and SEQ ID NO: 3; and the amino acid sequence encoded by papC and the nucleotide sequence of papC are each shown in SEQ ID NO: 6 and SEQ ID NO: 5.

Example 2

Expression of papA Gene in *Escherichia coli*

In order to obtain the translation region of the papA gene, PCR was carried out with the phage DNA derived from the positive clone shown in Example 1 as a template and oligonucleotides of SEQ ID NO: 9 and SEQ ID NO: 10 as primers. The PCR was carried out with KOD Dash (Toyobo Co., Ltd.) as DNA polymerase using the Gene Amp PCR System 9700 (Perkin-Elmer). A reaction solution containing 1 µl of phage DNA (equivalent to 1 µg), 5 µl of 10-fold concentrated reaction buffer attached to the enzyme, 5 µl of a 2 mM dNTP solution, 1 µl each of the above-mentioned primers prepared at a concentration of 100 pmol/µl, 5 µl of dimethyl sulfoxide (Wako Pure Chemical Industries, Ltd.), 1 µl of KOD Dash, and 31 µl of sterile water was made up into a total volume of 50 µl. The reaction was carried out by repeating incubation of 15 cycles of 30 seconds at 94° C., 2 seconds at 50° C. and 30 seconds at 72° C., after pretreatment at 94° C. for 5 minutes. The reaction solution thus obtained was extracted with phenol:chloroform:isoamyl alcohol (25:24:1) and precipitated with ethanol. The precipitate was redissolved in sterile water, and the DNA terminals were blunted using a DNA blunting kit (Takara Shuzo Co., Ltd.). Further, the 5' end was phosphorylated using T4 DNA kinase (Wako Pure Chemical Industries, Ltd.), after which agarose gel electrophoresis was carried out, a DNA fragment of approximately 2 kbp was isolated, recovered, and cloned into the SmaI site of plasmid pUC118 to obtain plasmid pUC118-papA.

The nucleotide sequence of the inserted fragment of pUC118-papA was determined using a fluorescent DNA sequencer ABI PRISM 310 Genetic Analyzer (Perkin-Elmer). As a result, it was revealed that cytosine at position 2043 in the nucleotide sequence of SEQ ID NO: 1 was replaced by adenine. Since this replacement was believed to be an error upon amplification of the DNA fragment by PCR and brought no change in the amino acid sequence to be encoded, the inserted fragment of pUC118-papA was used for the following experiment.

pUC118-papA was introduced into *Escherichia coli* JM110, and a plasmid was prepared from the resultant transformant using an ordinary method. After digesting with restriction enzyme BclI, agarose gel electrophoresis was carried out to isolate and recover a BclI DNA fragment of approximately 2 kbp.

Figure 2:
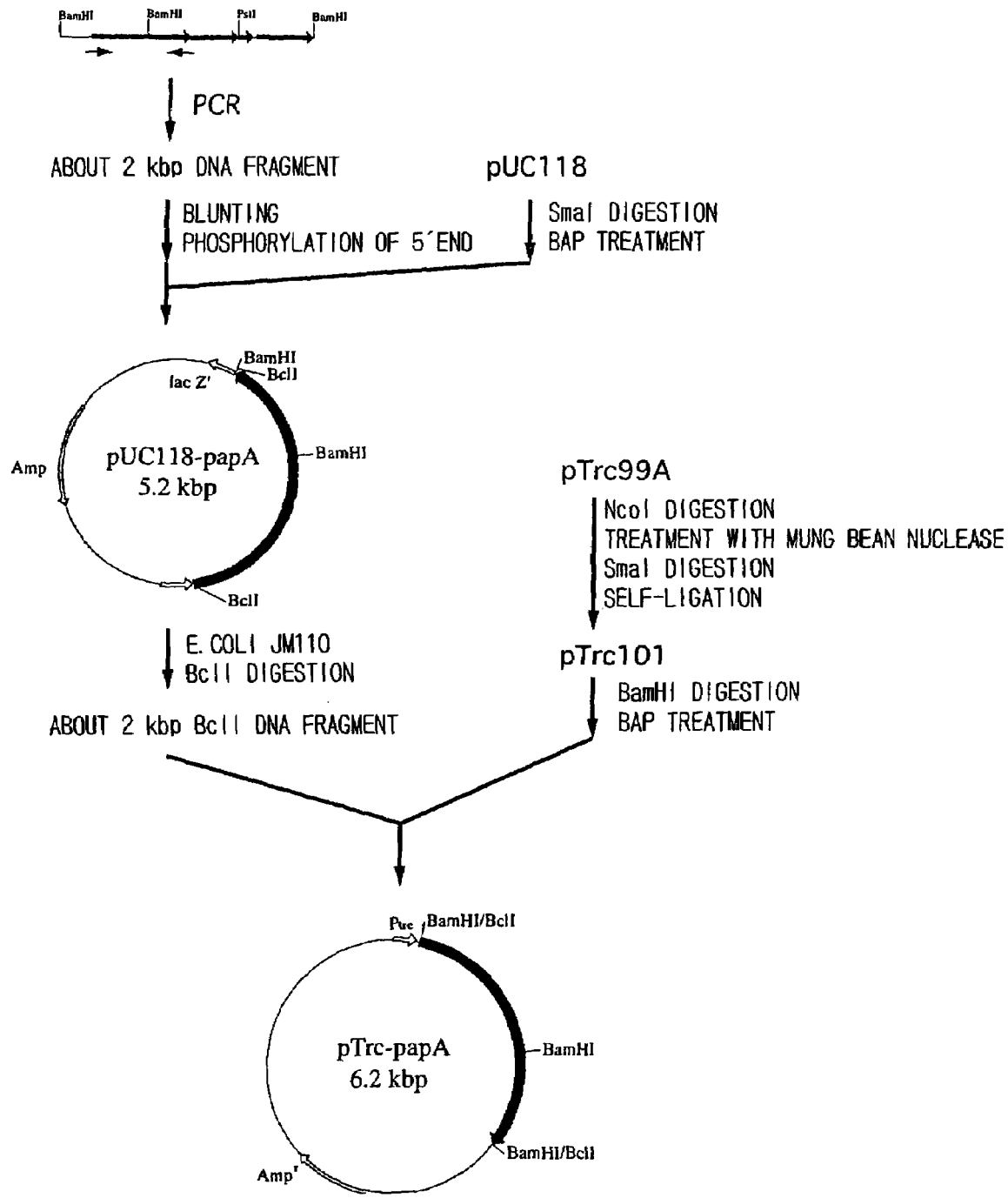
FIG. 2 shows the construction of plasmid pTrc-papA.

On the other hand, plasmid pTrc99A (Amersham Pharmacia Biotech) was digested with restriction enzyme NcoI, and the DNA terminals were blunted using Mung Bean Nuclease (Wako Pure Chemical Industries, Ltd.). The resultant fragment was further digested with restriction enzyme SmaI and then self-ligated using T4 DNA ligase to obtain plasmid pTrc101.

pTrc101 was digested with restriction enzyme BamHI and treated with alkaline phosphatase (Takara Shuzo Co., Ltd.), after which the resultant fragment was ligated to the above-mentioned 2 kbp BclI DNA fragment. A plasmid into which the papA gene was inserted in the correct orientation to the promoter contained in pTrc101 was selected and named pTrc-papA. FIG. 2 shows the process of the above-mentioned plasmid construction.

The *Escherichia coli* JM109 strain carrying pTrc-papA was cultured in an LB liquid medium (1% Bacto-tryptone, 0.5% yeast extract, 0.5% sodium chloride) supplemented with 100 µg/ml ampicillin, at 37° C. overnight. A 1 ml portion of the resultant culture was inoculated into 100 ml of the same medium, and incubation was carried out at 30° C. for 4 hours, after which 1 ml of 100 mM isopropylthiogalactoside (IPTG) was added, and incubation was further carried out at 30° C. for 3 hours. After incubation, cells were recovered from the culture by centrifugation, suspended in 4 ml of buffer solution for cell homogenization (50 mM Tris-HCl (pH 8.0), 5 mM EDTA, 10% glycerol) and then homogenized by ultrasonic treatment. After homogenization, the supernatant was recovered by centrifugation to obtain a cell extract. Further, the *Escherichia coli* JM109 strain carrying plasmid pTrc101 was treated in the same manner to prepare another cell extract.

The cell extracts thus prepared were measured for their enzymatic activity. Namely, 100 µl of the cell extract, 400 µl of distilled water, and 500 µl of a substrate solution [10 mM barium chorismate (Sigma), 10 mM glutamine (Wako Pure Chemical Industries, Ltd.), 10 mM magnesium chloride, 100 mM MOPS (Wako Pure Chemical Industries, Ltd.), pH 7.5] were mixed and reacted at 30° C. for 2 hours. After reaction, a portion of the reaction solution was analyzed using a full automatic amino acid analyzer JLC-500/V (JEOL, Ltd.).

Figure 3:
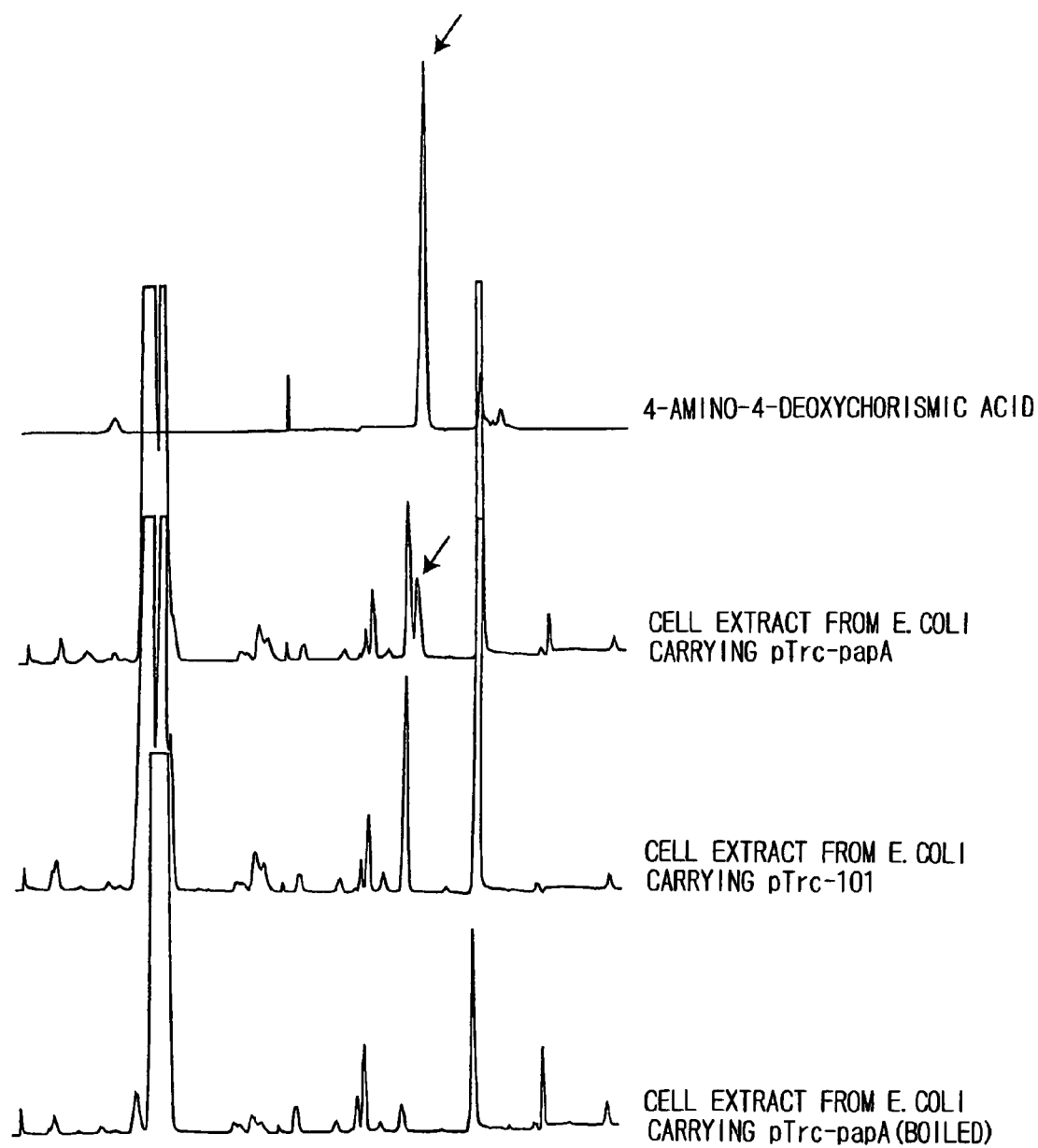
FIG. 3 shows the amino acid analyzer chromatograms used for detecting enzyme activity of a papA gene product.

As shown in FIG. 3, when the cell extract prepared from the *Escherichia coli* carrying pTrc-papA was used, a peak was detected on a position showing the same retention time with a standard for 4-amino-4-deoxychorismic acid synthesized according to the method of Chia-Yu P. Teng et al. (Chia-Yu P. Teng et al., J. Am. Chem. Soc., 107, 5008–5009, 1985). On the other hand, the peak on that position was not found when the cell extract was boiled or when the cell extract prepared from the *Escherichia coli* carrying pTrc101 was used. Thus, the papA gene was verified to encode 4-amino-4-deoxychorismic acid synthase.

Example 3

Expression of papB Gene in *Escherichia coli*

In order to obtain the translation region of the papA gene, PCR was carried out with the phage DNA derived from the positive clone shown in Example 1 as a template and oligonucleotides of SEQ ID NO: 11 and SEQ ID NO: 12 as primers. The PCR was carried out with KOD Dash (Toyobo Co., Ltd.) as DNA polymerase using Gene Amp PCR System 9700 (Perkin-Elmer). A reaction solution containing 1 μl of phage DNA (equivalent to 1 μg), 5 μl of 10-fold concentrated reaction buffer attached to the enzyme, 5 μl of a 2 mM dNTP solution, 1 μl each of the above-mentioned primers prepared at a concentration of 100 pmol/l, 5 μl of dimethyl sulfoxide (Wako Pure Chemical Industries, Ltd.), 1 μl of KOD Dash and 31 μl of sterile water was made up into a total volume of 50 μl. The reaction was carried out by repeating incubation of 15 cycles of 30 seconds at 94° C., 2 seconds at 50° C. and 30 seconds at 72° C., after pretreatment at 94° C. for 5 minutes. The reaction solution thus obtained was extracted with phenol:chloroform:isoamyl alcohol (25:24:1) and precipitated with ethanol. The precipitate was redissolved in sterile water and digested with restriction enzyme BamHI, after which agarose gel electrophoresis was carried out, and a DNA fragment of approximately 0.3 kbp was isolated according to an ordinary method to recover a DNA fragment.

pTrc101 was digested with restriction enzyme BamHI and treated with alkaline phosphatase (Takara Shuzo Co., Ltd.), after which the resultant fragment was ligated to the above-mentioned 0.3-kbp BamHI DNA fragment using T4 DNA ligase. A plasmid into which the papB gene was inserted in the correct orientation to the promoter contained in pTrc101 was selected and named pTrc-papB (FIG. 4). The nucleotide sequence of the inserted fragment of pTrc-papB was determined using a fluorescent DNA sequencer ABI PRISM 310 Genetic Analyzer (Perkin-Elmer) to verify that the sequence was identical with the nucleotide sequence of SEQ ID NO: 3.

The *Escherichia coli* JM109 strain carrying pTrc-papB was cultured in an LB liquid medium (1% Bacto-tryptone, 0.5% yeast extract, 0.5% sodium chloride) supplemented with 100 μg/ml ampicillin, at 37° C. overnight. A 1 ml portion of the resultant culture was inoculated into 100 ml of the same medium, and incubation was carried out at 37° C. for 2 hours, after which 1 ml of 100 mM isopropylthiogalactoside (IPTG) was added, and incubation was further carried out at 37° C. for 5 hours. After incubation, cells were recovered from the culture by centrifugation, suspended in 4 ml of buffer solution for cell homogenization (50 mMTris-HCl (pH 8.0), 5 mM EDTA, 10% glycerol), and then homogenized by ultrasonic treatment. After homogenization, the supernatant was recovered by centrifugation to obtain a cell extract. Further, the *Escherichia coli* JM109 strain carrying plasmid pTrc101 was treated in the same manner to prepare a cell extract.

The cell extracts thus prepared were measured for their enzymatic activity. Namely, 50 μl of the cell extract, 200 μl of distilled water, and 250 μl of a substrate solution [2 mg/ml 4-amino-4-deoxychorismic acid, 10 mM magnesium chloride, 100 mM MOPS (Wako Pure Chemical Industries, Ltd.), pH 7.5] were mixed and reacted at 30° C. for 1 hour. After reaction, a portion of the reaction solution was analyzed using a full automatic amino acid analyzer JLC-500/V (JEOL, Ltd.).

Figure 5:
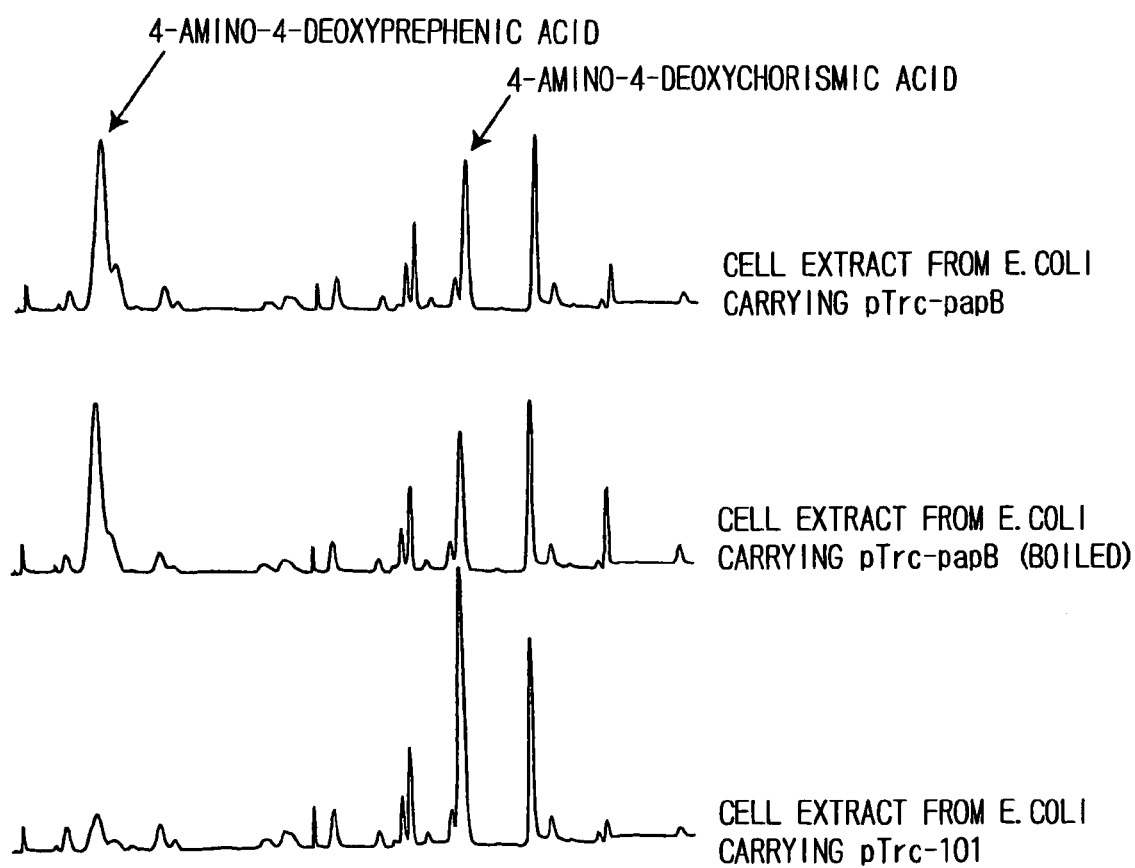
FIG. 5 shows the amino acid analyzer chromatograms used for detecting enzyme activity of a papB gene product.

As shown in FIG. 5, when the cell extract prepared from the *Escherichia coli* carrying pTrc-papB was used, the peak for 4-amino-4-deoxychorismic acid declined and the peak for 4-amino-4-deoxyprephenic acid was newly detected. A similar result was obtained when the cell extract boiled for 5 minutes was used.

On the other hand, when the cell extract prepared from the *Escherichia coli* carrying pTrc101 was used, there was no change in the peak for 4-amino-4-deoxychorismic acid, and the peak for 4-amino-4-deoxyprephenic acid was not detected. Thus, these results revealed that the papB gene encodes 4-amino-4-deoxychorismic acid mutase and that the 4-amino-4-deoxychorismic acid mutase encoded by the papB gene had heat-resistant activity which was not lost even after boiling for 5 minutes.

Example 4

Expression of papC Gene in *Escherichia coli*

In order to obtain the translation region of the papC gene, PCR was carried out using the phage DNA derived from the positive clone shown in Example 1 as a template and oligonucleotides of SEQ ID NO: 13 and SEQ ID NO: 14 as primers. The PCR was carried out with KOD Dash (Toyobo Co., Ltd.) as DNA polymerase using Gene Amp PCR System 9700 (Perkin-Elmer). A reaction solution containing 1 μl of phage DNA (equivalent to 1 μg), 5 μl of 10-fold concentrated reaction buffer attached to the enzyme, 5 μl of a 2 mM dNTP solution, 1 μl each of the above-mentioned primers prepared at a concentration of 100 pmol/μl, 5 μl of dimethyl sulfoxide (Wako Pure Chemical Industries, Ltd.), 1 μl of KOD Dash and 31 μl of sterile water was made up into a total volume of 50 μl. The reaction was carried out by repeating incubation of 15 cycles of 30 seconds at 94° C., 2 seconds at 50° C. and 30 seconds at 72° C., after pretreatment at 94° C. for 5 minutes. The reaction solution thus obtained was extracted with phenol:chloroform:isoamyl alcohol (25:24:1) and precipitated with ethanol. The precipitate was redissolved in sterile water, and digested with restriction enzyme BamHI, after which agarose gel electrophoresis was carried out, and a DNA fragment of approximately 1 kbp was isolated according to an ordinary method to recover a DNA fragment.

Plasmid pET-11c (Stratagene) was digested with restriction enzyme BamHI and treated with alkaline phosphatase (Takara Shuzo Co., Ltd.), after which the resultant fragment was ligated to the above-mentioned 1 kbp BamHI DNA fragment using T4 DNA ligase. A plasmid into which the papC gene was inserted in the correct orientation to the promoter contained in pET-11c was selected and named pET-papC.

The nucleotide sequence of the inserted fragment of pET-papC was determined using a fluorescent DNA sequencer ABI PRISM 310 Genetic Analyzer (Perkin-Elmer) to verify that the sequence was identical with the nucleotide sequence of SEQ ID NO: 5.

On the other hand, when the papC gene was expressed using pET-papC, evaluation of properties of papC gene products was expected to be difficult since the vector-derived peptide composed of 14 amino acids was added to the N-terminal side of the papC gene products. Therefore, pET-papC was digested with restriction enzyme NdeI, after which plasmid pET-papC1 was obtained by self-ligation using T4 DNA ligase. Use of pET-papC1 made it possible to produce papC gene products by themselves and not as fusion proteins. The above-mentioned plasmid construction process is shown in FIG. 6.

The *Escherichia coli* BL21 (DE3) strain carrying pET-papC1 was cultured in an LB liquid medium (1% Bacto-tryptone, 0.5% yeast extract, 0.5% sodium chloride) supplemented with 100 μg/ml ampicillin, at 37° C. overnight. A 1 ml portion of the resultant culture was inoculated into 100 ml of the same medium, and incubation was carried out at 37° C. for 2 hours, after which 1 ml of 100 mM isopropylthiogalactoside (IPTG) was added, and incubation was further carried out at 37° C. for 5 hours. After incubation, cells were recovered by centrifugation, suspended in 4 ml of buffer solution for cell homogenization (50 mM Tris-HCl (pH 8.0), 5 mM EDTA, 10% glycerol), and then homogenized by ultrasonic treatment. After homogenization, the supernatant was recovered by centrifugation to obtain a cell extract. Further, the *Escherichia coli* BL21 (DE3) strain carrying plasmid pET-11c was treated in the same manner to prepare a cell extract.

The cell extracts thus prepared were measured for their enzymatic activity. Namely, 40 µl of the cell extract, 10 µl of the cell extract which was prepared from the *Escherichia coli* carrying pTrc-papB described in Example 3 and boiled, 190 µl of distilled water, 10 µl of a 10 mM NAD solution, and 250 µl of a substrate solution [2 mg/ml 4-amino-4-deoxychorismic acid, 10 mM magnesium chloride, 100 mM MOPS (Wako Pure Chemical Industries, Ltd.), pH 7.5] were mixed and reacted at 30° C. for 1 hour. After reaction, a portion of the reaction solution was analyzed using a full automatic amino acid analyzer JLC-500/V (JEOL, Ltd.).

Figure 7:
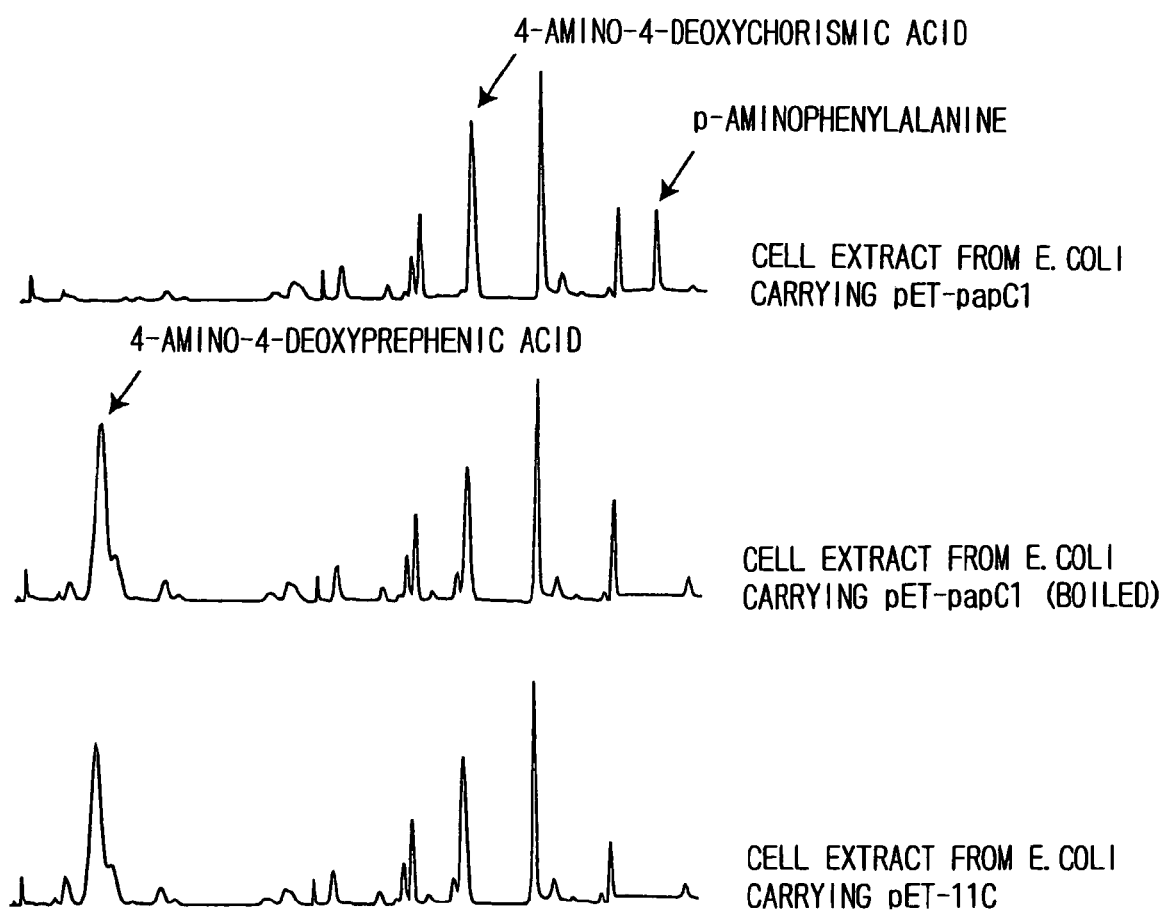
FIG. 7 shows the amino acid analyzer chromatograms used for detecting enzyme activity of a papC gene product.

As shown in FIG. 7, when the cell extract prepared from the *Escherichia coli* carrying pET-papC1 was used, the peak for 4-amino-4-deoxychorismic acid declined, and the peak for 4-amino-4-deoxyprephenic acid to be generated by the papB gene products disappeared. Since p-aminophenylpyruvic acid cannot be detected by the full automatic amino acid analyzer JLC-500/V, its synthesis could not directly be confirmed.

However, a peak for p-aminophenylalanine was detected. This was generated probably due to the transfer of an amino group of p-aminophenylpyruvic acid generated from papC gene products, by *Escherichia coli* aminotransferase. On the other hand, when the cell extract boiled and the cell extract which was prepared from the *Escherichia coli* carrying pET-11c were used, there was no change in the peak for 4-amino-4-deoxyprephenic acid generated from papB gene products. Thus, it was revealed that the papC gene coded for 4-amino-4-deoxyprephenic acid dehydrogenase.

Example 5

Figure 8:
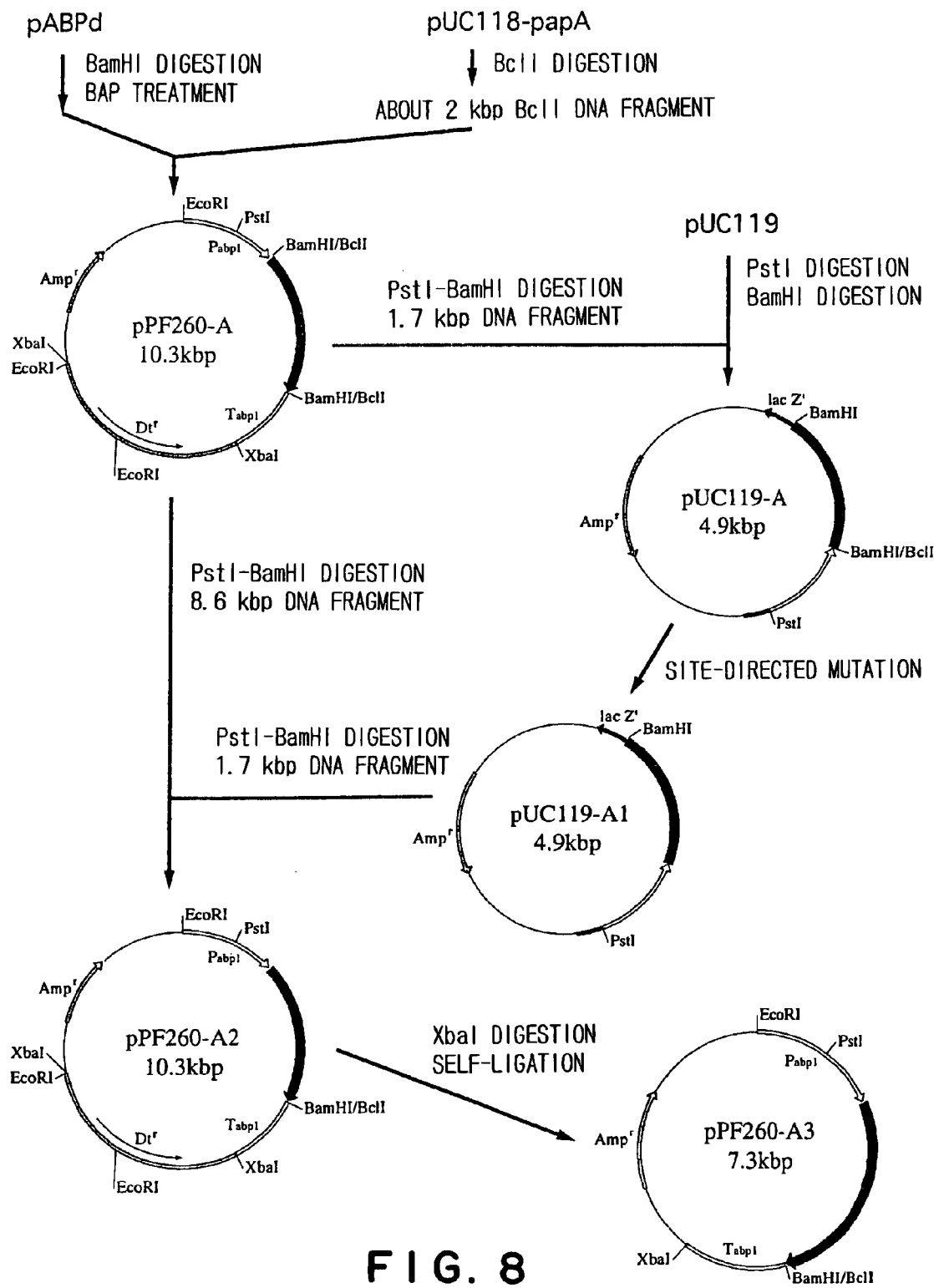
FIG. 8 shows the construction of plasmids pPF260-A2 and pPF260-A3.

Construction of Plasmids pPF260-A2 and pPF260-A3 for Introduction into PF1022 Producing-Microorganism Plasmids pPF260-A2 and pPF260-A3 for expressing the papA gene in a PF1022-producing microorganism were constructed as shown in FIG. 8.

An expression vector pABPd for a PF1022-producing microorganism was constructed, and then the DNA fragment obtained from plasmid pUC118-papA described in Example 2 was ligated to this vector to obtain an expression vector. More specifically, the expression vector was constructed as described below.

Isolation of Genomic DNA of Substance PF1022-Producing Microorganism

The genomic DNA of the strain PF1022-producing strain (FERM BP-2671) was isolated according to the method of Horiuchi et al. (H. Horiuchi et al., J. Bacteriol., 170, 272–278, 1988). More specifically, cells of the substance PF1022-producing strain (FERM BP-2671) were cultured for 2 days in a seed medium (2.0% soluble starch, 1.0% glucose, 0.5% polypeptone, 0.6% wheat germ, 0.3% yeast extract, 0.2% soybean cake, and 0.2% calcium carbonate; pH 7.0 before sterilization; see Example 1 in WO 97/00944), and the cells were recovered by centrifugation (3500 rpm, 10 minutes). The cells thus obtained were lyophilized, suspended in a TE solution, treated in a 3% SDS solution at 60° C. for 30 minutes, and then subjected to TE-saturated phenol extraction to remove the cell debris. The extract was precipitated with ethanol and treated with Ribonuclease A (Sigma) and Proteinase K (Wako Pure Chemical Industries, Ltd.), and then the nucleic acid was precipitated with 12% polyethylene glycol 6000. The precipitate was subjected to TE-saturated phenol extraction and ethanol precipitation, and the resulting precipitate was dissolved in a TE solution to obtain the genomic DNA.

Construction of Genome Library of Substance PF1022-Producing Microorganism

The genomic DNA derived from the substance PF1022-producing microorganism prepared as described above was partially digested with Sau3AI. The product was ligated to the BamHI arm of a phage vector, λEMBL3 Cloning Kit (Stratagene) using T4 ligase (Ligation Kit Ver. 2; Takara Shuzo Co., Ltd.). After ethanol precipitation, the precipitate was dissolved in a TE solution. The entire ligated mixture was used to infect *Escherichia coli* LE392 strain using a Gigapack III Plus Packaging Kit (Stratagene) to form phage plaques. The $1.3 \times 10^4$ ($2.6 \times 10^4$ PFU/ml) phage library obtained by this method was used for cloning of the Abp1 gene.

Cloning of the Abp1 Gene from the Genomic DNA Derived from Substance PF1022-Producing Microorganism A probe to be used was prepared by amplifying the translation region of the Abp1 gene by the PCR method. The PCR was carried out using the genomic DNA prepared from the substance PF1022-producing microorganism as described above as a template and synthetic primers 8-73U and 8-73R, according to a LETS GO PCR kit (SAWADY Technology). The PCR reaction for amplification was conducted by repeating 25 cycles of 30 seconds at 94° C., 30 seconds at 50° C., and 90 seconds at 72° C. DNA sequences of the 8-73U and 8-73R are as follows:

8-73U: CTCAAACCAGGAACTCTTTC (SEQ ID NO: 15)

8-73R: GACATGTGGAAACCACATTTG (SEQ ID NO: 16)

Figure 9:
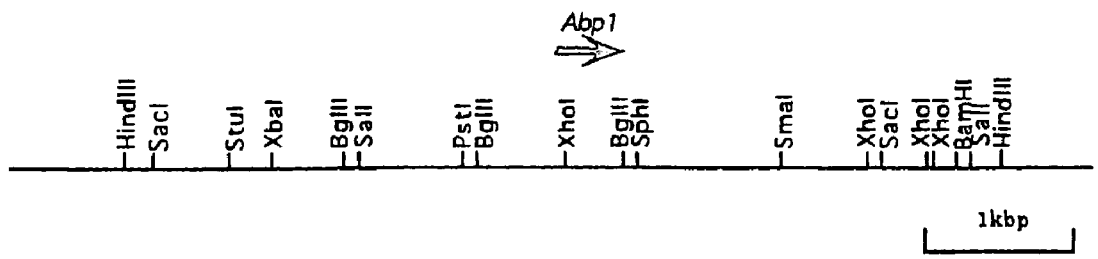
FIG. 9 shows the restriction map of the 6-kb HindIII fragment containing the Abp1 gene.

The PCR product thus obtained was labeled using an ECL Direct System (Amersham Pharmacia Biotech). The phage plaque prepared as described above was transferred to a Hybond N+ nylon transfer membrane (Amersham Pharmacia Biotech), and after alkaline denaturation, the membrane was washed with 5×SSC(SSC: 15 mM trisodium citrate, 150 mM sodium chloride) and dried to immobilize the DNA. According to the kit protocol, prehybridization (42° C.) was carried out for 1 hour, after which the above-mentioned labeled probe was added, and hybridization was carried out at 42° C. for 16 hours. The nylon membrane was washed according to the kit protocol described above. The washed nylon membrane was immersed for one minute in a detection solution and then photosensitized on a medical X-ray film (Fuji Photo Film Co., Ltd.) to obtain one positive clone. Southern blot analysis of this clone showed that a HindIII fragment of at least 6 kb was identical with the restriction enzyme fragment long of the genomic DNA. FIG. 9 shows the restriction map of this HindIII fragment. The HindIII fragment was subcloned into pUC119 to obtain pRQHin/119 for use of the following experiment.

19

Construction of Expression Vector

The promoter region and the terminator region of the AbpI gene were amplified by the PCR method using pRQHin/119 as a template. The PCR method was carried out using a PCR Super Mix High Fidelity (Lifetech Oriental Co., Ltd.) with primers ABP-Neco and ABP-Nbam for promoter amplification and ABP-Cbam and ABP-Cxba for terminator amplification. The amplification reaction was conducted by repeating 25 cycles of 30 seconds at 94° C., 30 seconds at 50° C. and 90 seconds at 72° C. The DNA sequences of ABP-Neco, ABP-Nbam, ABP-Cbam and ABP-Cxba are as follows:

ABP-Neco:    GGGGAATTCGTGGGTGGTGATAT-CATGGC (SEQ ID NO: 17)

ABP-Nbam: GGGGGATCCTTGATGGGTTTTGGG (SEQ ID NO: 18)

ABP-Cbam:    GGGGGATCCTAAACTCCCATCTATAGC (SEQ ID NO: 19)

ABP-Cxba:    GGGTCTAGACGACTCATTGCAGT-GAGTGG (SEQ ID NO: 20)

Figure 10:
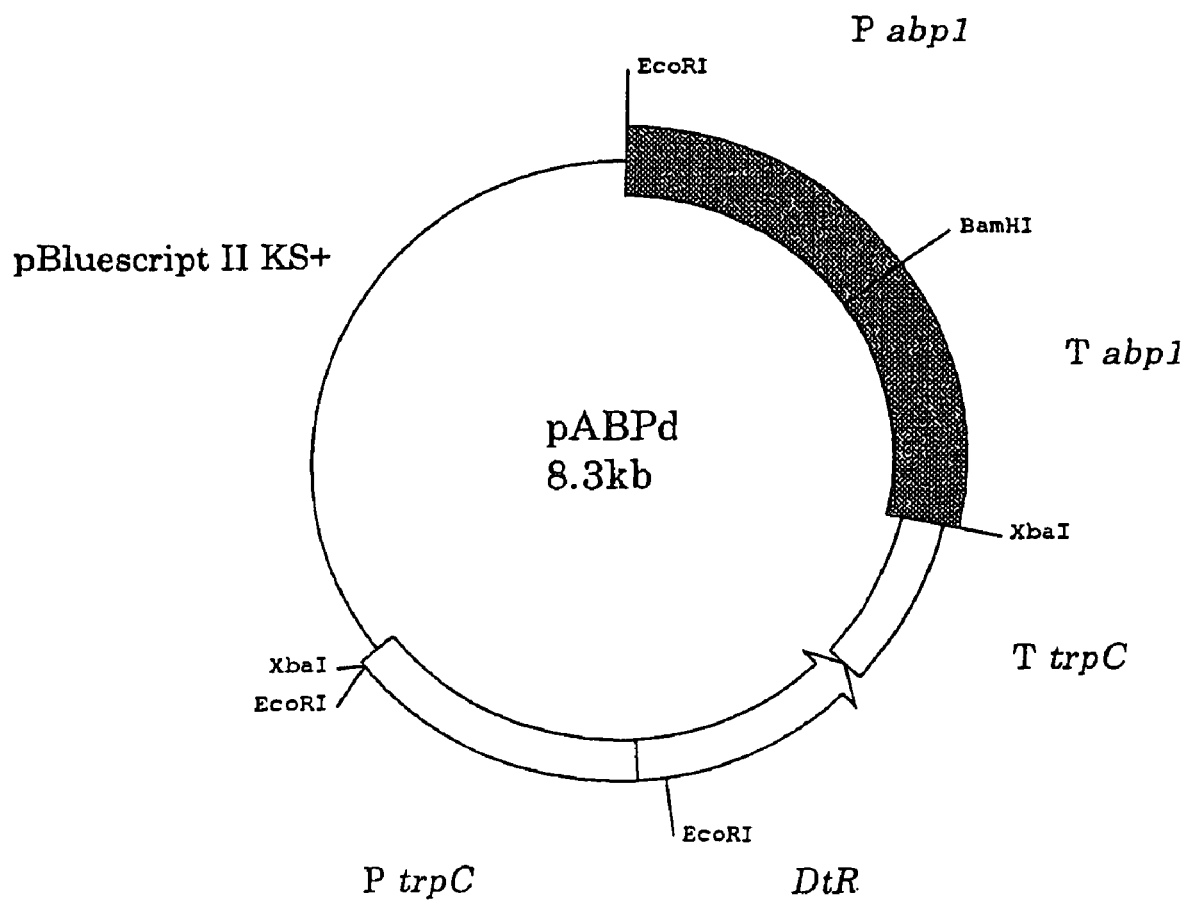
FIG. 10 shows the restriction map of pABPd.

Each PCR product was purified with a Microspin S-400 column (Amersham Pharmacia Biotech) and precipitated with ethanol, after which the promoter was double-digested with EcoRI and BamHI, the terminator was double-digested with BamHI and XbaI, and the resulting fragments were ligated one by one to pBluescript II KS+ previously digested with the same enzymes. The product was digested with XbaI, and a destomycin resistance cassette derived from pMKD01 (WO 98/03667) was inserted to construct pABPd (FIG. 10). pABPd has the promoter and terminator of the AbpI gene.

An approximately 2 kbp BclI DNA fragment was prepared from plasmid pUC118-papA described in Example 2. This fragment was inserted into the BamHI site of the expression vector pABPd for PF1022-producing microorganism to obtain plasmid pPF260-A.

Next, pPF260-A was double-digested with restriction enzymes PstI and BamHI to prepare a DNA fragment of approximately 1.7 kbp. This fragment was subcloned into PstI and BamHI sites of pUC119 to obtain plasmid pUC119-A. Treatment for site-directed mutagenesis was carried out with pUC119-A as a template DNA and the oligonucleotide of SEQ ID NO: 21 as a primer using a Muta-Gene in vitro Mutagenesis Kit (Bio-Rad) to obtain plasmid pUC119-A1.

Next, pUC119-A1 and pPF260-A were double-digested with restriction enzymes PstI and BamHI to prepare DNA fragments of approximately 1.7 kbp and approximately 8.6 kbp, and then these fragments were ligated to obtain plasmid pPF260-A2. Further, pPF260-A2 was digested with restriction enzyme XbaI and then self-ligated using T4 DNA ligase to obtain plasmid pPF260-A3.

Example 6

Figure 11:
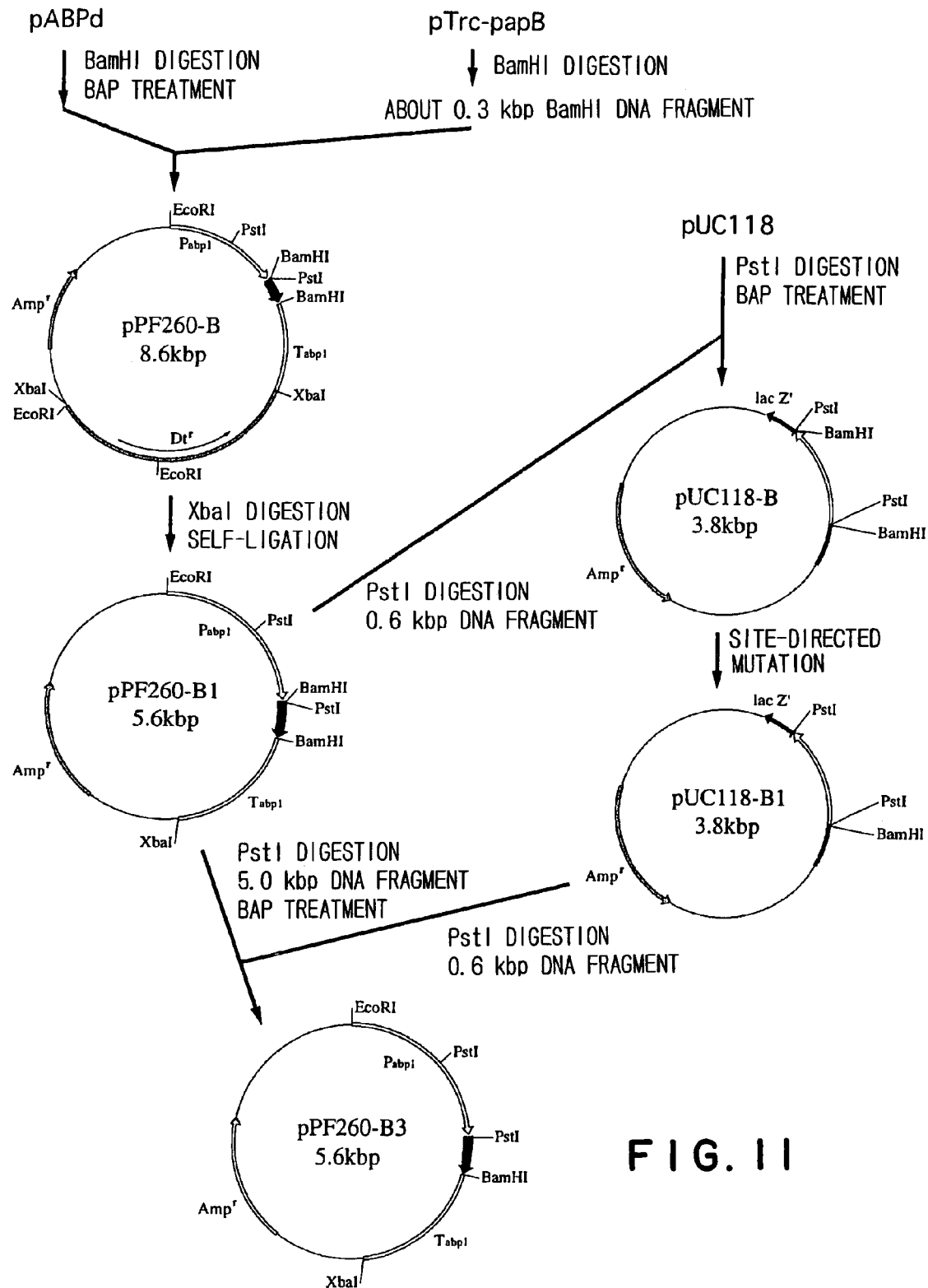
FIG. 11 shows the construction of plasmid pPF260-B3.

Construction of Plasmid pPF260-B3 for Introduction into PF1022-Producing Microorganism Plasmid pPF260-B3 for expressing the papB gene in a PF1022-producing microorganism was constructed as shown in FIG. 11.

An approximately 0.3 kbp BamHI DNA fragment was prepared from plasmid pTrc-papB described in Example 3. This fragment was inserted into the BamHI site of the expression vector pABPd (Example 5) to obtain plasmid pPF260-B. pPF260-B was digested with restriction enzyme XbaI and then self-ligated using T4 DNA ligase to obtain plasmid pPF260-B1.

Next, pPF260-B1 was digested with restriction enzyme PstI to prepare a DNA fragment of approximately 0.6 kbp. This fragment was subcloned into the PstI site of pUC118 in such a manner that the papB gene and the lacZ' gene aligned in the same direction to obtain plasmid pUC118-B. Treatment for site-directed mutagenesis was carried out with pUC118-B as a template DNA and the oligonucleotide of SEQ ID NO: 22 as a primer using a Muta-Gene in vitro Mutagenesis Kit (Bio-Rad) to obtain plasmid pUC118-B1.

Next, pUC118-B1 and pPF260-B1 were digested with restriction enzyme PstI to prepare DNA fragments of approximately 0.6 kbp and approximately 8.0 kbp, and then these fragments were ligated to obtain plasmid pPF260-B3.

Example 7

Construction of Plasmid pPF260-C3 for Introduction into PF1022-Producing Microorganism Plasmid pPF260-C3 for expressing the papC gene in a PF1022-producing microorganism was constructed as shown in FIG. 12.

An approximately 1 kbp BamHI DNA fragment was prepared from plasmid pET-papC described in Example 4. This fragment was inserted into the BamHI site of the expression vector pABPd (Example 5) to obtain plasmid pPF260-C pPF260-C was digested with restriction enzyme XbaI and then self-ligated using T4 DNA ligase to obtain plasmid pPF260-C1.

Next, pPF260-C1 was double-digested with restriction enzymes PstI and SphI to prepare a DNA fragment of approximately 1.7 kbp. This fragment was subcloned into the PstI and SphI sites of pUC118 to obtain plasmid pUC118-C. Treatment for site-directed mutagenesis was carried out with pUC118-C as a template DNA and the oligonucleotide of SEQ ID NO: 23 as a primer using a Muta-Gene in vitro mutagenesis kit (Bio-Rad) to obtain plasmid pUC118-C1.

Next, pUC118-C1 and pPF260-C1 were double-digested with restriction enzymes PstI and SphI to prepare DNA fragments of approximately 1.7 kbp and approximately 7.6 kbp, and then these fragments were ligated using T4 DNA ligase to obtain plasmid pPF260-C3.

Example 8

Transformation of PF1022-Producing Microorganism

A mixture of 1 µl of pPF260-A2, 3 µl of pPF260-A3, 3 µl of pPF260-B3, and 3 µg of pPF260-C3 was precipitated with ethanol and then redissolved in 10 µl of TE buffer (10 mM Tris-HCl (pH 8.0), 1 mM EDTA). The DNA solution thus prepared was used to transform a PF1022-producing microorganism according to the method described in Example 1 of WO 97/00944. More specifically, the PF1022-producing microorganism was cultured in the seed medium described in Example 5 at 26° C. for 48 hours. After cultivation, the resultant mycelia were collected by centrifugation at 3000 rpm for 10 minutes and washed with a 0.5 M sucrose solution. The mycelia thus obtained were subjected to protoplast generation by shaking in a 0.5M sucrose solution containing 3 mg/ml β-glucuronidase (Sigma), 1 mg/ml chitinase (Sigma) and 1 mg/ml zymolyase (Seikagaku Kogyo) at 30° C. for 2 hours. The mixture thus obtained was filtered to remove the cell debris. The protoplasts were washed twice by centrifugation (2500 rpm, 10 minutes, 4° C.) in an SUTC buffer solution (0.5M sucrose, 10 mM Tris-HCl (pH 7.5), 10 mM calcium chloride), and then a 1×10$^7$/ml protoplast suspension was prepared with the SUTC buffer solution.

The previously prepared plasmid DNA solution was added to 100 μl of the protoplast suspension, and the resultant mixture was allowed to stand under ice-cooling for 5 minutes. Then, 400 μl of a polyethylene glycol solution [60% polyethylene glycol 4000 (Wako Pure Chemical Industries, Ltd.), 10 mM Tris-HCl (pH 7.5), 10 mM calcium chloride] was added to this mixture, and the resultant admixture was allowed to stand under ice-cooling for 20 minutes.

The protoplasts treated as described above were washed with the SUTC buffer solution and resuspended in the same buffer solution. The resultant suspension was double-layered together with a potato dextrose soft agar medium onto a potato dextrose agar medium containing 100 μg/ml hygromycin B and 0.5M sucrose. Incubation was carried out at 26° C. for 5 days, and colonies appeared were deemed to be transformants.

Chromosomal DNAs were obtained from the resultant transformants, and PCR was carried out using them as a temperate DNA under the same conditions described in Examples 2, 3 and 4, except that 25 cycles were repeated, to detect the papA, papB and papC genes. As a result, the 55-65 strain (FERM BP-7255) was selected as a transformant into which all of the three genes were introduced.

Example 9

Cultivation of Transformed PF1022-Porducing Microorganism and Detection of PF1022 Derivative The transformant strain 55-65 (FERM BP-7255) selected in Example 8 and the parent strain were cultured as described in WO 97/20945. Namely, cells were cultured in the seed medium described in Example 5 at 26° C. for 2 days. A 2 ml portion of each resultant culture was inoculated into 50 ml of a production medium (0.6% wheat germ, 1.0% pharma media, 2.6% soluble starch, 6.0% starch syrup, 0.2% MgSO$_4$ 7H$_2$O, 0.2% NaCl), and incubation was further carried out at 26° C. for 6 days. After incubation, the resulting cells were collected from a 40 ml portion of the culture by centrifugation and then extracted with 30 ml of ethyl acetate. The extract was concentrated by drying and redissolved in 2 ml of acetonitrile. A 10 μl portion of the solution was subjected to HPLC analysis.

Figure 13:
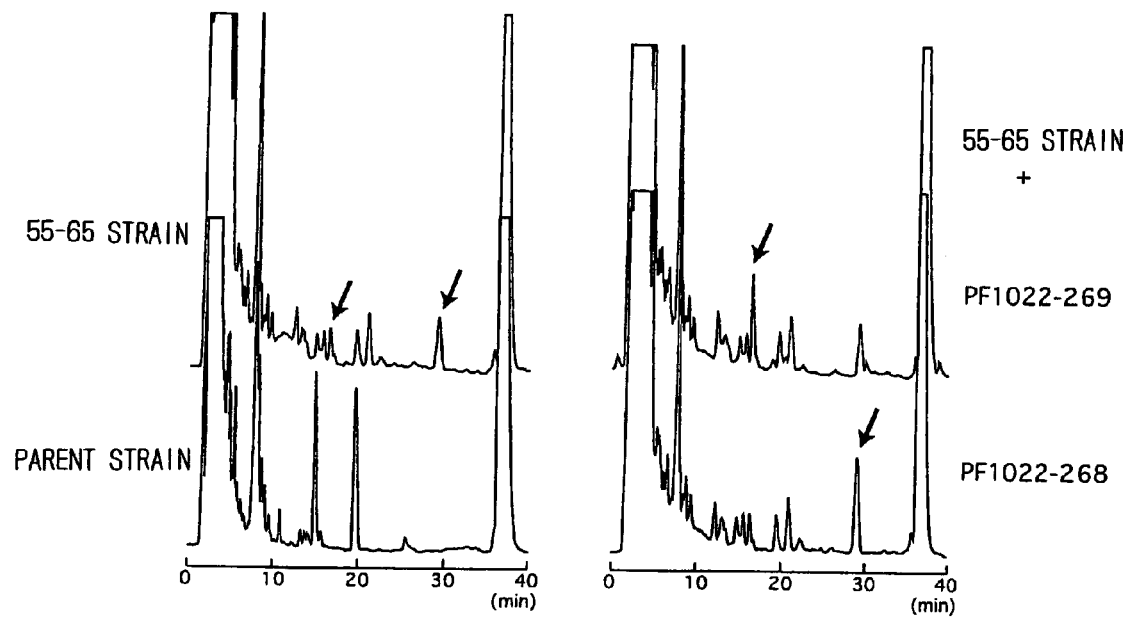
FIG. 13 shows the HPLC chromatograms used for detecting PF1022 derivatives in which a benzene ring is modified at the para-position with a nitro group or an amino group.
Figure 13:
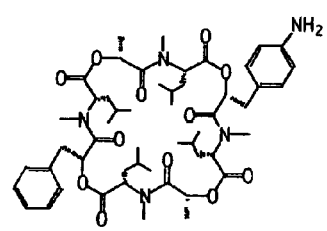
Figure 13:
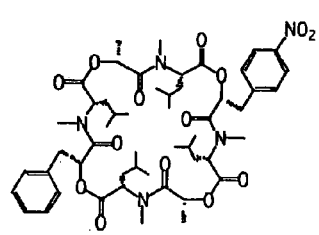

Conditions for HPLC analysis were as follows:

HPLC system—655A-11, Hitachi, Ltd.
  Column—Inertsil ODS-2, 4.6×250 mm
  Mobile phase—Acetonitorile:water=70:30
  Flow rate—1.0 ml/min
  Column temperature—40° C.
  Detector—870-UV, Nihon Bunko K. K.
  UV wave length—245 nm As shown in FIG. 13, the extract from the transformant strain 55-65 exhibited the peaks each showing the same retention time with PF1022-268 (cyclo[MeLeu-Lac-MeLeu-(O$_2$N)PhLac-MeLeu-Lac-MeLeu-PhLac]; Example 1 in WO 97/11064) and PF1022-269 (cyclo[MeLeu-Lac-MeLeu-(H$_2$N)PhLac-MeLeu-Lac-MeLeu-PhLac]; Example 2 in WO 97/11064). On the other hand, neither of these peaks was detected for the parent strain. Further, HPLC analysis using a mixture of the extract derived from the transformant and each standard verified that the peaks derived from the extract and the standard perfectly matched. Measurements of mass spectra using LC-MS (a quadrapole-type bench top LC/MS system NAVIGATOR with aQa™, Thermoquest) for the substances contained in these peaks agreed with those for the standards.

From the results above, it was revealed that the transformant 55-65 strain into which all of the three genes, i.e., the papA, papB and papC genes, were introduced produced the substance PF1022 derivatives in which a benzene ring is modified at the para-position with a nitro group or amino group.

The invention claimed is:

1. A transformant of a microorganism, wherein the transformant is produced by introducing (i) a polynucleotide encoding the amino acid sequence of SEQ ID NO: 2, (ii) a polynucleotide encoding the amino acid sequence of SEQ ID NO: 4, and (iii) a polynucleotide encoding the amino acid sequence of SEQ ID NO: 6, into the microorganism, wherein the microorganism to be transformed produces a peptide or a depsipeptide, which is substance PF1022 ([cyclo (D-lactyl-L-N-methylleucyl-D-3-phenyllactyl-L-N-methylleucyl-D-lactyl-L-N-methylleucyl-D-3-phenyllactyl-L-N-methylleucyl)]) represented by the following formula:

wherein the transformant produces a derivative of substance PF1022 represented by the following formula:

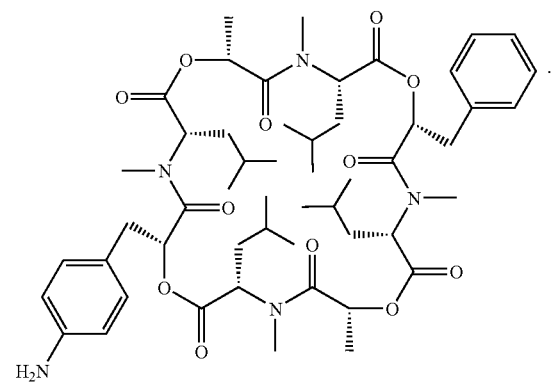

2. The transformant according to claim 1, wherein the peptide or the depsipeptide is synthesized from at least one molecule selected from the group consisting of phenylalanine, tyrosine, and phenyllactic acid.

3. The transformant according to claim 1, wherein the microorganism is transformed by introducing polynucleotides comprising: (i) the DNA sequence of SEQ ID NO: 1, (ii) the DNA sequence of SEQ ID NO: 3, and (iii) the DNA sequence of SEQ ID NO: 5 into the microorganism.

4. The transformant according to claim 1, wherein the transformant is strain 55-65 deposited with the National and Institute of Bioscience and Human-Technology under an accession number of FERM BP-7255.

5. The transformant according to claim 1 wherein substance PF1022 is synthesized by a substance PF1022-synthesizing enzyme from four molecules of L-leucine, two molecules of D-lactic acid and two molecules of D-phenyllactic acid.

6. A method for producing a peptide or a depsipeptide having a benzene ring skeleton substituted at the para-position with a nitro group or amino group, which comprises:
   culturing the transformant of claim 1 under conditions suitable for production of the peptide or the depsipeptide, and
   collecting the peptide or the depsipeptide.

7. A method for producing a substance PF1022 derivative, which comprises:
   culturing the transformant of claim 1 under conditions suitable for production of the substance PF1022 derivative, and
   collecting the substance PF1022 derivative.

8. An isolated polynucleotide encoding the amino acid sequence of SEQ ID NO: 2.

9. The polynucleotide according to claim 8, which comprises the DNA sequence of SEQ ID NO: 1.

10. An isolated polynucleotide encoding the amino acid sequence of SEQ ID NO: 4.

11. The polynucleotide according to claim 10, which comprises the DNA sequence of SEQ ID NO: 3.

12. An isolated polynucleotide encoding the amino acid sequence of SEQ ID NO: 6.

13. The polynucleotide according to claim 12, which comprises the DNA sequence of SEQ ID NO: 5.

14. A transformant of *Mycelia sterilia*, wherein the transformant is produced by transforming the *Mycelia sterilia* by introducing (i) a polynucleotide encoding the amino acid sequence of SEQ ID NO: 2, (ii) a polynucleotide encoding the amino acid sequence of SEQ ID NO: 4, and (iii) a polynucleotide encoding the amino acid sequence of SEQ ID NO: 6.

15. The transformant according to claim 14, wherein *Mycelia sterilia* is strain PF1022 deposited with the National Institute of Bioscience and Human-Technology under an accession number of FERM BP-2671.

16. The transformant according to claim 14, wherein *Mycelia sterilia* is transformed by introducing polynucleotides comprising (i) the DNA sequence of SEQ ID NO: 1, (ii) the DNA sequence of SEQ ID NO: 3, and (iii) the DNA sequence of SEQ ID NO: into the *Mycelia sterilia*.

17. The transformant according to claim 14, wherein the *Mycelia sterilia* to be transformed produces a substance PF1022 ([cyclo (D-lactyl-L-N-methylleucyl-D-3-phenyllactyl-L-N-methylleucyl-D-lactyl-L-N-methylleucyl-D-3-phenyllactyl-L-N-methylleucyl)]), represented by the following formula:

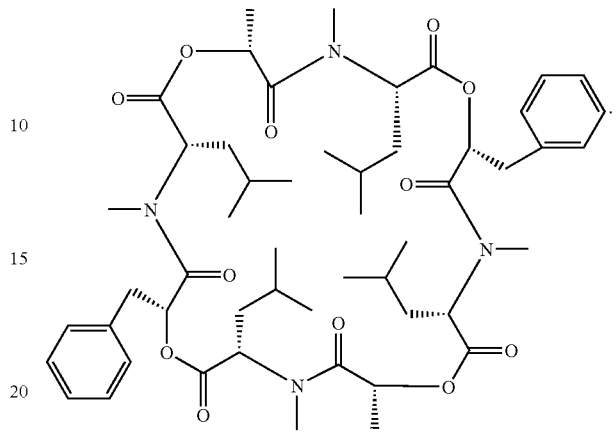

18. The transformant according to claim 17, wherein substance PF1022 is synthesized by a substance PF1022-synthesizing enzyme from four molecules of L-leucine, two molecules of D-lactic acid and two molecules of D-phenyllactic acid.

19. The transformant according to claim 14, wherein the derivative represented by the following formula:

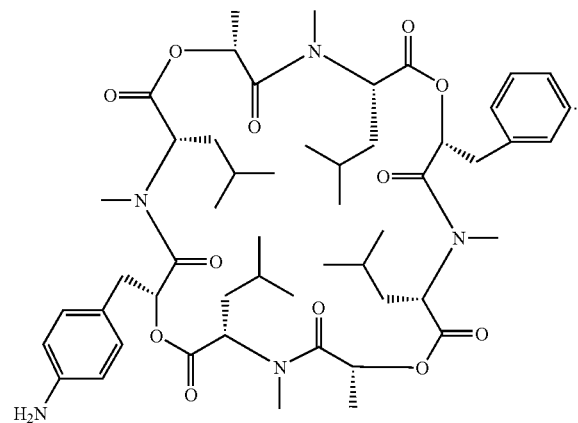

* * * * *